(12) United States Patent
Rothman et al.

(10) Patent No.: US 8,355,925 B2
(45) Date of Patent: Jan. 15, 2013

(54) METHODS OF ASSESSING RISK BASED ON MEDICAL DATA AND USES THEREOF

(75) Inventors: Michael J. Rothman, Hopewell Junction, NY (US); Steven I. Rothman, Sarasota, FL (US)

(73) Assignee: PeraHealth, Inc., Charlotte, NC (US)

( * ) Notice: Subject to any disclaimer, the term of this patent is extended or adjusted under 35 U.S.C. 154(b) by 499 days.

(21) Appl. No.: 12/582,942

(22) Filed: Oct. 21, 2009

(65) Prior Publication Data
US 2010/0100392 A1 Apr. 22, 2010

Related U.S. Application Data

(60) Provisional application No. 61/107,021, filed on Oct. 21, 2008, provisional application No. 61/107,028, filed on Oct. 1, 2008.

(51) Int. Cl.
*G06F 19/00* (2006.01)
*G06Q 10/00* (2006.01)
(52) U.S. Cl. .............................. 705/2; 705/3
(58) Field of Classification Search .................. 705/2, 3
See application file for complete search history.

(56) References Cited

U.S. PATENT DOCUMENTS

| | | | |
|---|---|---|---|
| 5,074,980 A | 12/1991 | Vasta-Russell et al. | |
| 5,850,339 A | 12/1998 | Giles | 364/148 |
| 5,860,917 A | 1/1999 | Comanor et al. | |
| 6,193,654 B1 * | 2/2001 | Richardson et al. | 600/300 |
| 6,336,903 B1 | 1/2002 | Bardy | |
| 6,438,419 B1 | 8/2002 | Callaway et al. | |
| 6,790,178 B1 | 9/2004 | Mault et al. | |
| 6,960,167 B2 | 11/2005 | Bardy | |
| 7,003,341 B2 | 2/2006 | Say et al. | |
| 7,031,857 B2 | 4/2006 | Tarassenko et al. | |
| 7,081,091 B2 | 7/2006 | Merrett et al. | |
| 7,213,009 B2 | 5/2007 | Pestotnik et al. | |
| 7,454,359 B2 | 11/2008 | Rosenfeld et al. | |

(Continued)

FOREIGN PATENT DOCUMENTS

GB 2 392 750 10/2004

(Continued)

OTHER PUBLICATIONS

Jones, "Glasgow Coma Scale," *The American Journal of Nursing*, 79(9), pp. 1551-1553 (Sep. 1979).

(Continued)

*Primary Examiner* — Robert Morgan
*Assistant Examiner* — Sean K Hunter
(74) *Attorney, Agent, or Firm* — Greenberg Traurig, LLP

(57) ABSTRACT

Methods of assessing risk based on medical data are disclosed herein. In an embodiment, a method of assessing risk associated with medical data includes creating a dataset representing a plurality of patients, the dataset comprising (x,y) pairs for each patient, wherein x represents the medical data collected at a first time, and wherein y is an outcome measurement collected at a second time; binning the (x,y) pairs to form a plurality of binned data sets; computing an average value for x and an average value for y for each binned data set; determining a minimum average value of y based on all of the average values of y; subtracting the minimum average value of y from each average value of y to get a new average value of y for each binned data set; and deriving a function for assessing risk associated with the medical data.

25 Claims, 12 Drawing Sheets

U.S. PATENT DOCUMENTS

| | | | |
|---|---|---|---|
| 7,853,456 | B2 | 12/2010 | Soto et al. |
| 8,092,380 | B2 | 1/2012 | Rothman et al. |
| 8,100,829 | B2 | 1/2012 | Rothman et al. |
| 2002/0026104 | A1 | 2/2002 | Bardy |
| 2003/0208106 | A1 | 11/2003 | Anderson et al. |
| 2003/0225315 | A1 | 12/2003 | Merrett et al. |
| 2005/0187796 | A1 | 8/2005 | Rosenfeld et al. |
| 2006/0161459 | A9 | 7/2006 | Rosenfeld et al. |
| 2006/0200009 | A1 | 9/2006 | Wekell et al. |
| 2006/0206012 | A1* | 9/2006 | Merrett et al. ............... 600/300 |
| 2006/0206013 | A1 | 9/2006 | Rothman et al. |
| 2006/0287906 | A1 | 12/2006 | McGillin |
| 2009/0105550 | A1 | 4/2009 | Rothman et al. |

FOREIGN PATENT DOCUMENTS

| | | |
|---|---|---|
| WO | WO 02/21313 | 3/2002 |
| WO | WO 03/082097 | 10/2003 |
| WO | WO 2006/093807 | 9/2006 |
| WO | WO2008/045577 | 4/2008 |
| WO | WO 2010/048282 | 4/2010 |

OTHER PUBLICATIONS

Rees, "Early Warning Scores," *Update in Anaesthesia World Anaesthesia*, 17(10), pp. 30-33 (2003).

Reintam et al., "Gastrointestinal Failure in Intensive Care: A Retrospective Clinical Study in Three Different Intensive Care Units in Germany and Estonia," *BMC Gastroenterology*, 6(19), doi:10.1186/1471-230X-6-19 (Jun. 22, 2006).

Ryan et al., "Setting Standards for Assessment of Ward Patients at Risk of Deterioration," *British Journal of Nursing*, 13(20), pp. 1186-1190 (Nov. 2004).

Office Action in U.S. Appl. No. 11/974,696 mailed May 25, 2010.

International Search Report based on PCT/US09/061478 dated Dec. 10, 2009.

International Search Report based on PCT/US06/06467 dated Sep. 14, 2007.

International Search Report based on PCT/US07/022054 dated Apr. 2, 2008.

Supplementary European Search Report based on PCT/US06/06467 dated Jul. 21, 2009.

Office Action in U.S. Appl. No. 11/974,696 mailed Jul. 1, 2009.

Office Action in U.S. Appl. No. 11/362,450 mailed May 20, 2009.

Final Office Action in U.S. Appl. No. 11/974,696 mailed Feb. 2, 2010.

Final Office Action in U.S. Appl. No. 11/362,450 mailed Apr. 2, 2010.

Abraham, Edward, "Glucose-6-Phosphate Dehydrogenase and Sepsis: The Jury is Still Out", Crit Care Med., Editorial, vol. 35, No. 2 (Feb. 2007) pp. 655-656.

Aiken et al., "Hospital Nurse Staffing and Patient Mortality, Nurse Burnout, and Job Dissatisfaction", JAMA, vol. 288, No. 16 (Oct. 23/30, 2002) pp. 1987-1993.

Alam, Hasan B., "To Cool or Not to Cool, That is the Question", Crit Care Med., Editorial, vol. 35, No. 2 (Feb. 2007) pp. 660-662.

Aneman et al., "The ERC Guidelines for Resuscitation 2005 and the Medical Emergency Team", Scand J Trauma Resusc Emerg Med, vol. 14 (2006), pp. 74-77.

Antman et al., "The TIMI Risk Score for Unstable Angina/Non-ST Elevation MI—A Method for Prognostication and Therapeutic Decision Making", JAMA, vol. 284, No. 7 (Aug. 16, 2000) pp. 835-842.

Asai, Takashi, "How Should We Use Prokinetic Drugs in Patients who are Intolerant to Enteral Feeding?", Crit Care Med., Editorial, vol. 35, No. 2 (Feb. 2007) pp. 650-651.

Baggs, Judith G., "Nurse-Physician Collaboration in Intensive Care Units", Crit Care Med., Editorial, vol. 35, No. 2 (Feb. 2007) pp. 641-642.

Baggs, Judith G., "Prognostic Information Provided During Family Meetings in the Intensive Care Unit", Crit Care Med., Editorial, vol. 35, No. 2 (Feb. 2007) pp. 646-647.

Bates et al., "Improving Safety with Information Technology", N. Engl J Med, vol. 348, No. 25 (Jun. 19, 2003) pp. 2526-2534.

Bensen et al., "To be or Not to be (In the Intensive Care Unit)-Is that a Question?", Crit Care Med., Editorial, vol. 35, No. 2 (Feb. 2007) pp. 647-648.

Berman et al., "Validation of the 2000 Bernstein-Parsonnet Score Versus the EuroSCORE as a Prognostic Tool in Cardiac Surgery", Ann Thorac Surg, vol. 86 (Feb. 2006) pp. 537-541.

Berms, John J., "Ischemia-Reperfusion: Putting the Pieces of the Puzzle Together", Crit Care Med., Editorial, vol. 34, No. 5 (May 2006) pp. 1570-1571.

Bion et al., "Improving the Reliability of Healthcare Systems' Responsiveness to the Needs of Acutely III Patients", Crit Care Med., Editorial, vol. 35, No. 2 (Feb. 2007) pp. 637-639.

Braden et al., "Braden Scale for Predicting Pressure Sore Risk" (1988).

Braden, Barbara J., "The Relationship Between Stress and Pressure Sore Formation", Ostomy Wound Management, vol. 44, Issue 3A, (Mar. 1998) pp. 26s-37s.

Brander et al.. "Exophageal and Transpulmonary Pressure Help Optimize Mechanical Ventilation in Patients with Acute Lung Injury", Crit Care Med., Editorial, vol. 34, No. 5 (May 2006) pp. 1556-1558.

Brennan et al., "Accidental Deaths, Saved Lives, and Improved Quality", N Engl J Med, vol. 353, No. 13 (Sep. 29, 2005) pp. 1405-1409.

Clark et al., "Concurrent Prediction of Hospital Mortality and Length of Stay From Risk Factors on Admission", vol. 37, No. 3 (Jun. 2002) pp. 631-645.

Clinton et al., "Making Patient Safety the Centerpiece of Medical Liability Reform", N. Engl J Med, vol. 354, No. 21 (May 25, 2006), pp. 2205-2208.

Cole, Randolph P., "Predicting Response to Fluid Administration: Something Old, Something New?", Crit Care Med., Editorial, vol. 34, No. 5 (May 2006) pp. 1559-1560.

Coimbra, Raul, "Salt in the Vein, Good for the Brain . . . ", Grit Care Med., Editorial, vol. 35, No. 2 (Feb. 2007) pp. 659-660.

Cretikos et al., "The Objective Medical Emergency Team Activation Criteria: A Case-Control Study", Resuscitation, vol. 73, No. 1 (Apr. 2007) pp. 62-72.

Crippen, David, "Comfortably Numb in the Intensive Care Unit", Crit Care Med., Editorial, vol. 34, No. 5 (May, 2006) pp. 1558-1559.

Cuthbertson, B.H., "Can Physiological Variables and Early Warning Scoring Systems Allow Early Recognition of the Deteriorating Surgical Patient?", Crit Care Med, vol. 35, No. 2 (Feb. 2007) pp. 402-409.

Cuthbertson, B.H., "Editorial II: Outreach Critical Care-Cash for No Questions", British Journal of Anesthesia, Editorial II, vol. 90, No. 1 (Jan. 2003) pp. 4-6.

DeVita et al., "Findings of the First Consensus Conference on Medical Emergency Teams", Crit Care Med, vol. 34, No. 9 (Sep. 2006) pp. 2463-2478.

Dupuydt et al., "Antiobiotic Therapy for Ventilator-Associated Pneumonia: De-Escalation in the Real World", Crit Care Med., Editorial, vol. 35, No. 2 (Feb. 2007) pp. 632-633.

Egevad et al., "Prognostic Value of the Gleason Score in Prostate Cancer" BJI International, vol. 89, Issue 6 (Apr. 9, 2002) pp. 538-542.

Engle, Toby R. Md "Electrocardiographic Diagnosis of Coronary Syndromes in the Critical Care Unit", Crit Care Med., Editorial, vol. 34, No. 5 (May 2006) pp. 1546-1547.

Epstein, Scott K, MD "Preventing Prostextubation Respiratory Failure", Crit Care Med., Editorial, vol. 34, No. 5 (May 2006) pp. 1547-1548.

Erikkson, Urs, "Chlamydia and Myocarditis: An Old Bug Bugging Seriously", Crit Care Med., Editorial, vol. 35, No. 2 (Feb. 2007) pp. 665.

Finster et al., "The Apgar Score has Survived the Test of Time", Anesthesiology, vol. 102, No. 4 (Apr. 2005) pp. 855-857.

Forster et al., "Adverse Events Among Medical Patients After Discharge", CMAJ, vol. 170, No. 3 (Feb. 3, 2004) pp. 345-349.

Fraser et al., "Comfort without Coma: Changing Sedation Practices", Crit Care Med., Editorial, vol. 35, No. 2 (Feb. 2007) pp. 635-637.

Friedman et al., "The Rate and Cost of Hospital Readmissions for Preventable Conditions", MCR&R, vol. 61, No. 2 (Jun. 2004), pp. 225-240.

Gao et al., "Systematic Review and Evaluation of Physiological Track and Trigger Warning Systems for Identifying At-Risk Patients on the Ward", Intensive Care Med, vol. 33, No. 4 (Apr. 2007) pp. 667-679.

Gentilello, Larry M., "Alcohol and the Intensive Care Unit: It's Not Just an Antiseptic", Crit Care Med., Editorial, vol. 35, No. 2 (Feb. 2007) pp. 627-628.

Gogbashian et al., "EuroSCORE: A Systematic Review of International Performance", European Journal of Cario-thoracic Surgery, vol. 25 (Feb. 2004) pp. 695-700.

Goldhill, David R., "Editorial: of Missiles and Medicine: Early Warning Systems", Anaesthesia, vol. 61, No. 3 (Feb. 14, 2006) pp. 209-214.

Goldhill et al., "Physiological Values and Procedures in the 24 h Before ICU Admission from the Ward", Anaesthesia, vol. 54, Issue 6 (Jun. 1999) pp. 529-534.

Goldstein, Brahm, "How Do We Get From Here to There? A Pathway for Trial Design in Complex Systems Analysis", Crit Care Med., Editorial, vol. 35, No. 2 (Feb. 2007) pp. 656-658.

Goodacre et al., "Prediction of Mortality Among Emergency Medical Admissions", Emerg Med J, vol. 23, No. 5 (May 2006), pp. 372-375.

Greenhalgh, David G., "Hypoxic Pulmonary Vasoconstriction After Combined Burn and Inhalation Injury", Crit Care Med., Editorial, vol. 34, No. 5 (May 2006) pp. 1562-1563.

Groeneveld et al. "Catecholamines, Parasympathetic Stimuli, or Cortisol for Overwhelming Sepsis", Crit Care Med., Editorial, vol. 34, No. 5 (May 2006) pp. 1549-1550.

Hager, et al. "Customizing Lung-Protective Mechanical Ventilation Strategies", Crit Care Med., Editorial, vol. 34, No. 5 (May 2006) pp. 1554-1555.

Hart, G.K., "Editorial: Antecedents to Hospital Deaths: All in Good Time", Internal Medical Journal, vol. 31, No. 6 (Aug. 2001) pp. 321.

Herlitz et al., "Characteristics and Outcome Among Patients Suffering In-Hospital Cardiac Arrest in Monitored and Non-Monitored Areas", Resuscitation, vol. 48, No. 2 (Feb. 2001) pp. 125-135.

Herlitz et al., "Very High Survival Among Patients Defibrillated at an Early Stage After In-Hospital Ventricular Fibrillation on Wards With and Without Monitoring Facilities", Resuscitation, vol. 66, No. 2 (Aug. 2005) pp. 159-166.

Hillman et al., "Antecedents to Hospital Deaths", Internal Medical Journal, vol. 31, No. 6 (Dec. 21, 2001) pp. 343-348.

Hillman et al., "Introduction of the Medical Emergency Team (MET) System: a Cluster-Randomised Controlled Trial", Lancet, vol. 365 (Jun. 18, 2005), pp. 2091-2097.

Hovda et al., "Oxidative Need and Oxidative Capacity Following Traumatic Brain Injury", Crit Care Med., Editorial, vol. 35, No. 2 (Feb. 2007) pp. 663-664.

Hravnak, Marilyn, "Electronic Integrated Monitoring of Medical Emergency Team Calls to a Step Down Unit", This is Biosigns Presentation, (Jun. 2006).

Jacobs, et al., "Increasing Vigilance on the Medical/Surgical Floor to Improve Patient Safety", Journal of Advanced Nursing, vol. 57, No. 5 (Mar. 2007) pp. 472-781.

Kause et al., "A Comparison of Antecedents to Cardiac Arrests, Deaths and Emergency Intensive Care Admissions in Australia and New Zealand, and the United Kingdom-the Academia Study", Resuscitation, vol. 62, No. 3 (Sep. 2004) pp. 275-282.

Knaus et al., "The Apache III Prognostic System. Risk Prediction of Hospital Mortality for Critically III Hospitalized Adults", Chest, vol. 100 (1991) pp. 1619-1636.

Kramer et al. "Uniform Patient Assessment for Post-Acute Care", Division of Health Care Policy and Research, UCDHSC, Aurora, CO (Jan. 25, 2006), pp. 1-135.

Knoefel, Wolfram Trudo, "The Peritonitis Dilemma: Better Safe Than Sorry or Wait for the Cat to Jump", Crit Care Med., Editorial, vol. 35, No. 2 (Feb. 2007) pp. 648-649.

Kruger et al., "Nonuse of Statins-A New Risk Factor for Infectious Death in Cardiovascular Patients", Crit Care Med., Editorial, vol. 35, No. 2 (Feb. 2007) pp. 631-632.

Krumholz et al., "Randomized Trial of an Education and Support Intervention to Prevent Readmission of Patients with Heart Failure", JACC, vol. 39, No. 1 (Jan. 2, 2002) pp. 83-89.

Kucher et al., "Electronic Alerts to Prevent Venous Thromboembolism Among Hospitalized Patients", vol. 352, No. 10 (Mar. 10, 2005) pp. 969-977.

Landesberg et al., "Silent Myocardial Ischemia in the Noncoronary Intensive Care Unit: A New Frontier?", Crit Care Med., Editorial, vol. 35, No. 2 (Feb. 2007) pp. 629-630.

Lemaire, Francois, "Low-Dose Perfluorocarbon: A Revival for Partial Liquid Ventilation", Crit Care Med., Editorial, vol. 35, No. 2 (Feb. 2007) pp. 662-663.

Leonhardt, David, "Why Doctors So Often Get it Wrong", New York Times, (Feb. 22, 2006), available at http://www.nytimes.com/2006/02/22/business/22leonhardt.html?_r=1&pagewanted=print&oref=slogin (last visited Jan. 14, 2008).

Lohr et al., "Smart Care Via a Mouse, but What Will it Cost?", New York Times, (Aug. 20, 2006), available at http://www.nytimes.com/2006/08/20/business/yourmoney/20info.html?_r=1&pagewanted=print&oref=slogin (last visited Jan. 14, 2008).

Luce, John. M., "Acknowledging our Mistakes", Crit Care Med., Editorial, vol. 34, No. 5 (May 2006) pp. 1575-1576.

Luna, Carlos M., "Modulating the Oral Colonization with Povidone-iodine Antiseptic: A New Approach for an Old Controversy", Crit Care Med., Editorial, vol. 34, No. 5 (May 2006) pp. 1572-1573.

Machado, Roberto F., "Nitric-Oxide Based Therapies in Sickle Cell Disease: The Evidence Continues to Mount", Crit Care Med., Editorial, vol. 35, No. 2 (Feb. 2007) pp. 654-655.

Marini, John, J.. Lessons Learned: The Conditional Importance of High Positive End-Expiratory Pressure in Acute Respiratory Distress Syndrome, Crit Care Med., Editorial, vol. 34, No. 5 (May 2006) pp. 1540-1542.

Marshall et al., Multiple Organ Dysfunction Score: A Reliable Descriptor of a Complex Clinical Outcome, Crit. Care Med., vol. 23, No. 10 (Oct. 1995) pp. 1638-1652.

Mimoz et al., "Prevention of Ventilator-Associated Pneumonia: Do Not Forget to Disinfect the Mouth", Crit Care Med., Editorial, vol. 35, No. 2 (Feb. 2007) pp. 668-669.

Morgan et al., "An Early Warning Scoring System for Detecting Developing Critical Illness", Clinical Intensive Care, vol. 8, No. 2 (Apr. 1997), pp. 11.

Morris, Alan H., MD "Extracorporeal Support and Patient Outcome: Credible Causality Remains Elusive", Crit Care Med., Editorial, vol. 34, No. 5 (May 2006) pp. 1551-1552.

Mundow, Anna, "A Cut Above?", Irish Times, (May 26, 2007).

Muhl, Heiko, "Controlling the Cytokine Storm y Insulin: Glycogen Synthase Kinase-3 as a Target in Systemic Inflammation", Crit Care Med., Editorial, vol. 34, No. 5 (May 2006) pp. 1567-1569.

Nasraway Stanley A., Jr., "'Search and Destroy' for Methicillin-Resistant *Staphylococcus aureus* in the Intensive Care Unit: Should This Now be the Standard of Care?", Crit Care Med., Editorial, vol. 35, No. 2 (Feb. 2007) pp. 642-644.

Needham et al., "Critically Appraise Before you Believe: The Quality of Meta-Analyses in Critical Care Medicine", Crit Care Med., Editorial, vol. 35, No. 2 (Feb. 2007) pp. 666-667.

Nozari, Ala, "Tuning Up the Compression and Applying the Choke for Better Horsepower in Resuscitation", Crit Care Med., Editorial, vol. 34, No. 5 (May 2006) pp. 1563-1564.

O'Rourke, Michael F., "Pressure Pulse Waveform Analysis in Critical Care", Crit Care Med., Editorial, vol. 34, No. 5 (May 2006) pp. 1569-1570.

Papadakos, Peter J., MD "The Long and Short of Sedation Practices: Daily Interruption or Bolus Sosing?", Crit Care Med., Editorial, vol. 34, No. 5 (May 2006) pp. 1544-1545.

Parienti et al., "Viral Pneumonia and Respiratory Sepsis: Association, Causation, or it Depends", Crit Care Med., Editorial, vol. 35, No. 2 (Feb. 2007) pp. 639-640.

Parissopoulos et al., "Critical Care Outreach and the Use of Early Warning Scoring Systems; A Literature Review", Icus Nurs Web J, Issue 21, (Jan.-Mar. 2005), pp. 1-13.

Pear, Robert, "A.M.A. To Develop Measurement of Quality of Medical Care", New York Times, (Feb. 21, 2006), available at http://www.nytimes.com/2006/02/21/politics/21docs.html? pagewanted=print (last visited May 12, 2010).

Plost et al., "Family Care in the Intensive Care Unit: The Golden Rule, Evidence, and Resources", Crit Care Med., Editorial, vol. 35, No. 2 (Feb. 2007) pp. 669-670.

Pollack et al., "Prism III: An Updated Pediatric Risk of Mortality Score", Crit. Care Med., vol. 24, Issue 5, (May 1996) pp. 743-752.

Rand Corporation, "An Argument for Electronic Records", New York Times, (Aug. 19, 2006).

Reilly et al., "Translating Clinical Research into Clinical Practice: Impact of Using Prediction Rules to Make Decisions", Ann Intern Med, vol. 144, No. 3 (Feb. 7, 2006) pp. 201-209.

Rexius et al., "A Simple Score to Assess Mortality Risk in Patients Waiting for Coronary Artery Bypass Grafting", Ann Thorac Surg, vol. 81, No. 2 (Feb. 2006) pp. 577-582.

Sarasota's Guidelines for When to Call a Rapid Response Team (as seen by BJR posted on East Tower, floor 9), (Apr. 18, 2007).

Sheridan, Rob, "Reducing Blood Loss in Burn Care", Crit Care Med., Editorial, vol. 35, No. 2 (Feb. 2007) pp. 665.

Sirio, Carl A. "Critical Care Performance Measurement: The Time has Come for All", Crit Care Med., Editorial, vol. 34, No. 5 (May 2006) pp. 1538-1539.

Southern et al., "Hospitals Care and Length of Stay in Patients Requiring Complex Discharge Planning and Close Clinical Monitoring", Arch Intern Med, vol. 167, No. 17 (Sep. 24, 2007) pp. 1869-1874.

Song et al., "Alveolar Hemostatis in Patients with Species-Specific Bacterial-Mediated Ventilator-Associated Pneumonia", Crit Care Med., Editorial, vol. 35, No. 2 (Feb. 2007) pp. 652-653.

Subbe et al., "Effect of Introducing the Modified Early Warning Score on Clinical Outcomes, Cardio-Pulmonary Arrests and Intensive Care Utilisation in Acute Medical Admissions" Anaesthesia, vol. 58, No. 8 (Jul. 14, 2003) pp. 797-802.

Subbe et al., "Validation of a Modified Early Warning Score in Medical Admissions", Q J Med, vol. 94, No. 10 (Oct. 2001) pp. 521-526.

Tarassenko et al., "Integrated Monitoring and Analysis for Early Warning of Patient Deterioration", British Journal of Anesthesia, vol. 97, No. 1 (May 17, 2006) pp. 64-68.

Teasdale et al., "Revisiting the Glasgow Coma Scale and Coma Score", Intensive Care Med, vol. 26, No. 2 (Feb. 2000) pp. 153-154.

Tirschwell, David, "Improved Prediction of Awakening or Nonawakening in Severe Anoxic Coma Using Tree-Based Classification", Crit Care Med., Editorial, vol. 34, No. 5 (May 2006) pp. 1573-1574.

Tsai, Amy G., "Can the Effects of Vasoactivity of Molecular Hemoglobin-Based Plasma Expanders be Ignored", Crit Care Med., Editorial, vol. 34, No. 5 (May 2006) pp. 1566-1567.

van der Voot, P.H.J., "Diagnostic and Scientific Dilemma: The Ischemic Bowel", Crit Care Med., Editorial, vol. 34, No. 5 (May 2006) pp. 1561-1562.

van der Voot, P.H.J., "The Incomplete Puzzle of Vasoactive Medication in (Abdominal) Sepsis", Crit Care Med., Editorial, vol. 34, No. 5 (2006) pp. 1565-1566.

Van Venrooij et al., "International Prostate Symptom Score and Quality of Life Assessment Versus Urodynamic Parameters in Men with Benign Prostatic Hyperplasia Symptoms", The Journal of Urology, vol. 153 (May 1995) pp. 1516-1519.

Wagner, Douglas P., Ph.D., "What Accounts for the Difference between Observed and Predicted?", Crit Care Med., Editorial, vol. 34, No. 5 (May, 2006) pp. 1552-1553.

Wang et al., "Is Inter-Alpha Inhibitor Important in Sepsis", Crit Care Med., Editorial, vol. 35, No. 2 (Feb. 2007) pp. 634-635.

Watkinson et al., "A Randomised Controlled Trial of the Effect of Continuous Electronic Physiological Monitoring on the Adverse Event Rate in High Risk Medical and Surgical Patients", Anesthesia, vol. 61, No. 11 (Oct. 16, 2006) pp. 1031-1039.

Webster, Nigel R., "Monitoring the Critically Ill Patient", J.R. Coll. Surg. Edinb., vol. 44 (Dec. 1999) pp. 386-393.

Weisberg, Lawrence, S., "Sic Transit Acetylcysteine?", Crit Care Med., Editorial, vol. 35, No. 2 (Feb. 2007) pp. 644-645.

Werdan, Karl, MD "Immunoglobulin Treatment in Sepsis—Is the Answer 'No'?", Crit Care Med., Editorial, vol. 34, No. 5 (May 2006) pp. 1542-1544.

Winters et al., "Rapid Response Systems: A Systematic Review", Crit Care Med, vol. 35, No. 5, (May 2007), pp. 1238-1243.

Winters et al., "Rapid Response Teams-Walk, Don't Run", JAMA, vol. 296, No. 13, (Oct. 4, 2006), pp. 1645-1647.

Young, G. Bryan, "Intensive Care Unit/Critical Illness Myopathy: Toward a Unifying Hypothesis", Crit Care Med., Editorial, vol. 35, No. 2 (Feb. 2007) pp. 628-629.

Zimmerman et al., "Acute Physiology and Chronic Health Evaluation (APACHE) IV: Hospital Mortality Assessment for Today's Critically Ill Patients", Crit Care Med, vol. 3, No. 5 (May 2006) pp. 1297-1310.

Office Action in U.S. Appl. No. 11/362,450 mailed Mar. 30, 2011.

Office Action in U.S. Appl. No. 11/974,696 mailed Jun. 10, 2011.

* cited by examiner

METHODS OF ASSESSING RISK BASED ON MEDICAL DATA AND USES THEREOF

RELATED APPLICATIONS

This application claims the benefit of and priority to U.S. Provisional Application Ser. No. 61/107,021, filed Oct. 21, 2008, and U.S. Provisional Application Ser. No. 61/107,028, filed Oct. 21, 2008, the entirety of these applications are hereby incorporated herein by reference.

FIELD

The embodiments disclosed herein relate to methods of assessing risk based on medical data and uses thereof, and more particularly, to deriving functions for assessing risk associated with medical data.

BACKGROUND

Despite an intense focus on the safety and quality of the care provided in hospitals in the United States generated by reports from the Institute of Medicine, progress is frustratingly slow. One weakness in our hospital systems is the lack of a clear-cut, reliable assessment of a patient's risk that can be used to communicate among healthcare professionals. Current nursing staffing and physician-coverage practices have accentuated the need for a tool that can highlight changes in a patient's risk not easily apparent to a caregiver unfamiliar with that patient.

Catastrophic deterioration of patients in a hospital is frequently preceded by documented deterioration of physiological parameters. Many systems quantify patient risk for a particular disease or condition. Currently, there is an emphasis on a group of models that quantify risk across diseases, but with a limited goal: to identify patients at extreme risk for cardiac or respiratory arrest. These systems are used to trigger medical emergency teams (MET), rapid response teams (RRT), or critical care outreach (CCO). Currently, most RRT in the United States are triggered by one parameter at a time, and that parameter often represents a significant change in a particular vital sign. For example, a significant change in blood pressure might trigger a call to the RRT, or a significant change in skin color might trigger a call. In some cases, a general feeling that something is not right might lead to a call. Failure of clinical staff to respond to deterioration of respiratory or cerebral function and increase levels of medical intervention will put patients at risk of cardio-respiratory arrest. Inappropriate action in response to observed abnormal physiological and biochemical variables might lead to avoidable death. Suboptimal care prior to admission to a critical care unit can lead to increased mortality.

Because of resource limitations, the number of patients that can be monitored and treated in intensive care units (ICUs) and high dependency units (HDUs) is restricted. The selection of patients who might benefit from critical care is therefore crucial. Identifying medical in-patients at risk of deterioration at an early stage by means of simple protocols based on physiological parameters may reduce the number of pre-ICU resuscitations One thing that a few hospitals have done is to employ an Early Warning System (EWS) as a means for deciding whether a patient needs to be transferred to the ICU. Other hospitals have developed a Modified Early Warning System (MEWS). Both existing systems typically use a small number of factors such a pulse, blood pressure, temperature, and respiratory rate. For each factor, a partial score is given, and all of these are then tabulated into a total score, which in turn is expressed as a binary recommendation: whether or not to move the patient into the ICU; no other action is suggested, no other information is obtained.

Such systems determine a patient's need to be transferred to the ICU by providing an emergency alert. However, these systems do not provide assistance to the doctor or nurse in helping to anticipate and thereby avoid medical crises, nor are they helpful to the clinical researcher in evaluating the efficacy of procedures and treatments. They convey no health trend information. Also, they are limited in the number of factors analyzed and thus are not very sensitive to general health conditions.

SUMMARY

Methods of assessing risk based on medical data and uses thereof are disclosed herein.

According to aspects illustrated herein, there is provided a method of assessing risk associated with medical data that includes creating, by a computer, a dataset representing a plurality of patients, the dataset comprising (x,y) pairs for each patient, wherein x represents the medical data collected at a first time, and wherein y is an outcome measurement collected at a second time; binning, by a computer, the (x,y) pairs to form a plurality of binned data sets; computing, by a computer, an average value for x and an average value for y for each binned data set; determining, by a computer, a minimum average value of y based on all of the average values of y; subtracting, by a computer, the minimum average value of y from each average value of y to get a new average value of y for each binned data set; and deriving, by a computer, a function for assessing risk associated with the medical data. In an embodiment, the deriving of the function includes computing, by a computer, a first function defined from average minimum value of x to average maximum value of x; adding, by a computer, a second constant function to the first function, wherein the second constant function covers values of x less than the average minimum value of x; and adding, by a computer, a third constant function to the first function and the second constant function, wherein the third constant function covers values of x greater than the average maximum value of x.

According to aspects illustrated herein, there is provided a method of determining an overall risk inherent in a patient's current condition that includes receiving, by a computer, a plurality of medical data from an admitted patient; converting, by a computer, each of the admitted patient's medical data to Health Score values using a set of functions, wherein each of the functions defines risk associated with each of the medical data; combining, by a computer, the Health Score values; generating, by a computer, a Health Score from the combined data, the Health Score representing the admitted patient's health; and displaying, by a computer, the Health Score. In an embodiment, the set of functions is derived using the following steps: (a) creating, by a computer, a dataset representing a plurality of discharged patients, the dataset comprising (x,y) pairs for each patient, wherein x represents a single type of medical data collected at a first time, and wherein y is an outcome measurement collected at a second time; (b) binning, by a computer, the (x,y) pairs to form a plurality of binned data sets; (c) computing, by a computer, an average value for x and an average value for y for each binned data set; (d) determining, by a computer, a minimum average value of y based on all of the average values of y; (e) subtracting, by a computer, the minimum average value of y from each average value of y to get a new average value of y for each binned data set; (f) deriving, by a computer, a function for assessing risk associated with the single type of medical data; and (g) repeating steps (a)-(f) for other types of medical data to derive the set of functions.

According to aspects illustrated herein, there is provided a method of assessing excess risk associated with medical data that includes creating, by a computer, a dataset representing a plurality of patients, the dataset comprising (x,y) pairs for each patient, wherein x represents the medical data collected at a first time, and wherein y is an outcome measurement collected at a second time; binning, by a computer, the (x,y) pairs to form a plurality of binned data sets; computing, by a computer, an average value for x and an average value for y for each binned data set; determining, by a computer, a minimum average value of y based on all of the average values of y; subtracting, by a computer, the minimum average value of y from each average value of y to get a new average value of y for each binned data set; and deriving, by a computer, a function for assessing excess risk associated with the medical data. In an embodiment, the deriving of the function includes computing, by a computer, a first function defined from average minimum value of x to average maximum value of x; adding, by a computer, a second constant function to the first function, wherein the second constant function covers values of x less than the average minimum value of x; and adding, by a computer, a third constant function to the first function and the second constant function, wherein the third constant function covers values of x greater than the average maximum value of x.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

Figure 1:
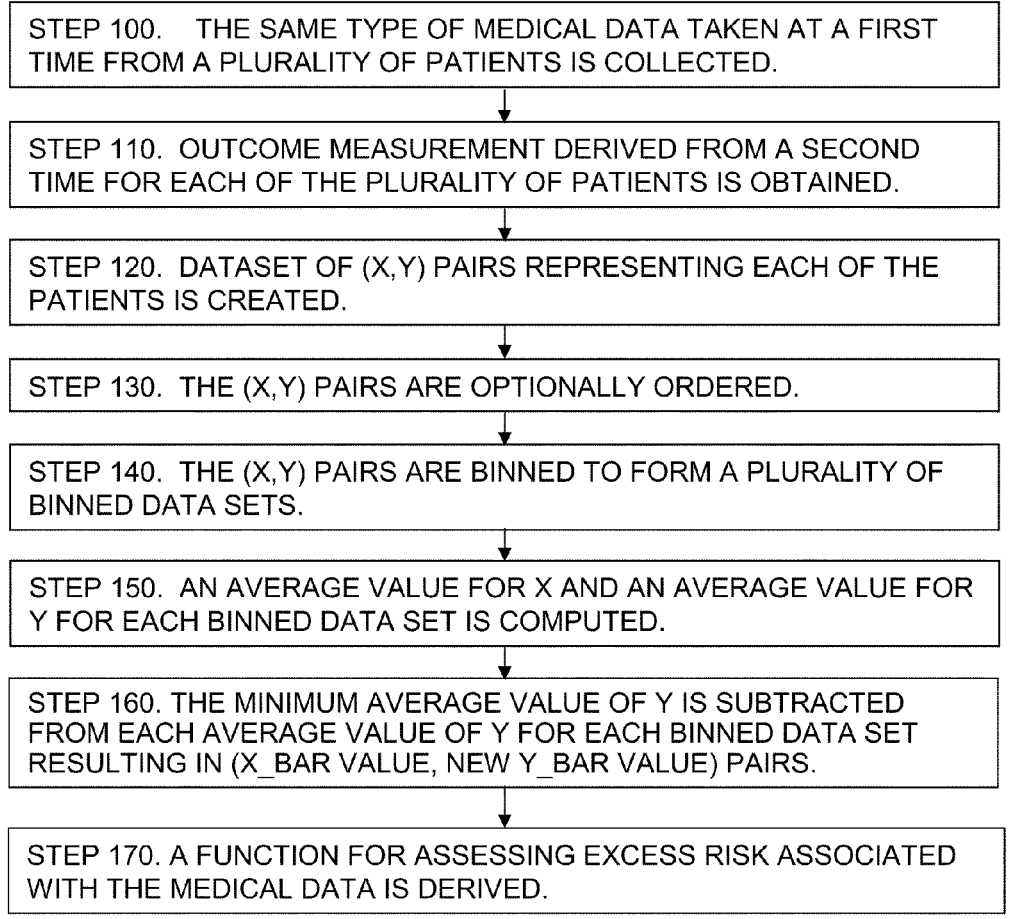
FIG. 1 is a flow chart showing an embodiment of a method of assessing risk associated with at least one type of medical data due to deviation from normative values.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

One of the problems in delivery of effective medical treatment in hospitals is the quality and continuity of patient care. A typical patient, undergoing a serious procedure in a hospital, may easily see five or more physicians during a stay, and also many nurses and other supporting personnel. Maintaining a complete medical record for each patient ("charting") swallows huge amounts of nursing time without providing any guidance to the medical staff on how to improve the patient's care. The present state of the art in medical care within hospitals makes very little use of the medical record, which is so bulky and awkward that it can only be quickly perused by doctors on their rounds. Such reading of the chart makes it almost impossible to evaluate treatment modalities or to detect a patient's declining health in time for intervention (before a crisis).

During a week's hospital stay, each patient may see many doctors and many nurses. This makes it extremely difficult to provide continuity of care. Every different caregiver must understand the medical record to give the patient optimum care, but the form and content of present-day medical charting provides no help. Each subsequent physician, whether a consultant or a shift replacement, is ill-prepared by current methods to obtain a correct overall medical status of the patient, thus posing a danger to the continued care of the patient, particularly in the recovery stages after serious operations For example, an attending physician, while making rounds in a hospital, may stop in on a patient, see that the patient has good color and is sitting up in bed, and thusly satisfied, goes on to his next appointment. However, if that patient had been walking up and down the corridors two days ago, and now cannot get out of bed, there is a problem. The patient may be experiencing a major and potentially life-threatening complication.

The essence of this problem is that, although all the medical information is recorded, it is not easily understood. After just a few days in the hospital, a patient may have twenty or even one hundred pages in their hospital record, including physician progress reports, nursing evaluations, records of vital signs, test results, heart monitoring information, and so on. However, even if every doctor and nurse who saw the patient were fully aware of the material in this record, it would not be enough to allow for the best medical care because it is very difficult to detect trends in such voluminous data.

The result of this arrangement has been to allow a number of patients in recovery, post-operation or procedure, to deteriorate to the point of medical crisis before addressing their problems. This causes a serious drain to the resources of the hospital, and unnecessary pain and suffering, even death. It is particularly bothersome because many of the conditions that lead to such crises can easily be avoided if the failing condition of a patient were discovered hours or days earlier.

One thing that a few hospitals have done is to employ an Early Warning System (EWS) as a means for deciding whether a patient needs to be transferred to the ICU. Other hospitals have developed a Modified Early Warning System (MEWS). Both existing systems typically use a small number of factors such a pulse, blood pressure, temperature, and respiratory rate. For each factor, a partial score is given, and all of these are then tabulated into a total score, which in turn is expressed as a binary recommendation: whether or not to move the patient into the ICU; no other action is suggested, no other information is obtained.

Such systems determine a patient's need to be transferred to the ICU by providing an emergency alert. However, these systems do not provide assistance to the doctor or nurse in helping to anticipate and thereby avoid medical crises, nor are they helpful to the clinical researcher in evaluating the efficacy of procedures and treatments. They convey no health trend information. Also, they are limited in the number of factors analyzed and thus are not very sensitive to general health conditions. For example, in the above-described example of a patient sitting up and alert in bed, this type of evaluation completely misses the patient's declining health. Because the patient still does have acceptable vital signs, he is not moved to the ICU, and neither the EWS, nor the MEWS, would generate an alert. However, if during the two previous days, this same patient had been walking around the hospital halls, but is now not able to rise from a bed, an important medical decline has happened, possibly one that will lead to a medical crises if not attended to, even though his major vital signs are still acceptable. Some embodiments of the present disclosure address these omissions, providing new continual, sensitive tools for improving medical care.

Embodiments of the present disclosure relate to the development of a general measure of risk for a hospitalized patient, sensitive to the full range of patient conditions, available for use throughout a hospital, independent of diagnosis, which can be used to assess a patient's state, and more particularly to a system and methods for recognizing downtrends which may indicate the onset of a complication, and to aid in communication of this information across staff handoffs.

After being admitted to a hospital, and during a typical hospital stay, various tests, such as blood or urine tests, may be conducted to evaluate a patient and collect data. Similarly, the patient may be hooked up to various medical devices/monitors to collect raw medical data. The patient may be asked about eating habits, mood, vaccinations, drugs taken, problems with walking, the amount of help needed with daily activities, and living arrangements. The patient may be asked a standard series of questions to evaluate mental function. A physical assessment may be performed on the patient to gather information about a patient's physiological, psychological, sociological, and spiritual status. A comprehensive patient assessment yields both subjective and objective findings. Subjective findings are obtained from the health history and body systems review. Objective findings are collected from the physical examination. Subjective data are apparent only to the patient affected and can be described or verified only by that patient. Pain, itching, and worrying are examples of subjective data.

Although objective data has been used in the past to generate a single number representing a patient's health, subjective data, such as nursing assessments, may be very significant in predicting the health of a patient. Subjective data may include variables, which may require human evaluation or assessment, rather than collecting a numerical value, such as blood pressure, heart rate, and other measurable factors. Subjective data includes information commonly collected in nursing assessments. Examples of subjective data may include standards which are determined by a nurse after assessing a variety of factors in a category, such as cardiac standard (which may be include factors, such as pulse rate in beats per minute, warmth and dryness of ski, blood pressure, and/or symptoms of hypotension), food/nutrition standard ((which may be include factors, such as ability to chew and/or swallow, manual dexterity, and/or consumption of daily diet as ordered, observed or stated), gastrointestinal standard (which may be include factors, such as feel and appearance of the abdomen, bowel sounds, nausea or vomiting, continence and/or bowel patterns), genitourinary standards (which may be include factors, such as voids, continence, urine color and/or smell as observed or stated, and/or urinary catheter), musculoskeletal standards (which may be include factors, such as ability to move all extremities independently and/or perform functional activities as observed or stated, including use of assistive devices), neurological standards (which may be include factors, such as alertness, orientation to persons, place, time and situation and/or speech coherence), pain standard (which may be include factors, such as pain/VAS level and/or chronic pain management), peripheral vascular standard (which may be include factors, such as normal appearance and feel (e.g., warm and pink) of extremities, capillary refill, peripheral pulses, edema, numbness and/or tingling), psycho-social standard (which may be include factors, such as appropriateness of behavior to situation, expressed concerns and fears being addressed and/or support system), respiratory standard (which may be include factors, such as respirations at rest, bilateral breath sounds, nail beds and mucous membranes, and/or look and feel of sputum), safety/fall risk standard (which may be include factors, such as risk of patient to self and/or others), and/or skin/tissue standard (which may be include factors, such as skin CD&I, reddened areas, alertness, cooperation and ability to reposition self independently, and/or Braden scale). Any or all of the above standards can be determined by a nurse using a pass/fail system. Even though these standards may be binary assessments, the transition from passing a standard to failing a standard can be very predictive in indicating the health of a patient. For example, if a patient moves from failing two standards, to failing five standards, to failing 7 standards, the patient may be going through a very serious decline in health, even if the patient's vital signs are relatively normal or not changing.

In an embodiment, the present disclosure relates to systems and methods for assessing the risk inherent in medical data, and the sum is used as a measure of patient risk. The presently disclosed systems and methods uses medical data heretofore ignored. In an embodiment, the systems and methods disclosed herein addresses patients for whom the set of models used for Rapid Response Teams are insensitive. In addition to vital signs, the commonly used inputs to such models, the disclosed systems and methods use nursing assessments and relate the nursing assessments to various physiological standards. In addition to monitoring patients who are gravely ill, the disclosed system is sensitive along the full range of potential patient risk, that is, a downtrend in a patient who is not in imminent danger of needing a move to the ICU can be sensed.

In an embodiment, medical data available from an electronic medical record (EMR)—a computerized legal medical record created in an organization that delivers care—can be collected and processed, without requiring any additional work from the hospital staff, using a method of the present disclosure, presenting a visual summary of the risk inherent in each medical data. FIG. 1 is a flow chart showing an embodiment of a method of assessing risk associated with at least one type of medical data due to deviation from normative values. The steps performed in FIG. 1 can be carried out by a computer or computing device having one or more processors, memory, software (including, but not limited to, programs, data, and protocols) and hardware (including, but not limited to, circuits, displays, power supplies, cables, keyboards, printers and mice). In step 100, the same type of medical data taken at a first time from a plurality of patients is collected, for example, from an electronic medical record (EMR) by a computer. In an embodiment, the first time corresponds to the time the patient is discharged from a facility of care (e.g., hospital, nursing home). In an embodiment, the type of medical data that is collected is a continuous variable measured at the time of discharge from a facility of care. In an embodiment, the type of medical data that is collected is an ordinal score generated at the time of discharge from a facility of care. In an embodiment, the type of medical data that is collected is a categorical class determined at the time of discharge from a facility of care. In an embodiment, the type of medical data that is collected is a binary assessment taken at the time of discharge from a facility of care.

In step 110, an outcome measurement derived from a second time for each of the plurality of patients is obtained by a computer. In an embodiment, the outcome measurement represents a mortality of each of the patients, for example, as determined by reviewing death records available at the National Institute of Standards and Technology. In an embodiment, the outcome measurement is determined at a second time corresponding to ninety-days post discharge. In an embodiment, the outcome measurement is determined at a second time corresponding to one-year post discharge. The idea is that a patient is discharged from the facility of care only when the patient is stable enough to be discharged. The patient may be discharged to home, or to a skilled nursing facility, or the patient may die, but there is a significance to this final value that allows the comparison with an outcome, such as one-year mortality. In an embodiment, the outcome measurement is either a "yes" or "no" answer. For example, was this patient dead one-year post discharge? In step 120, a dataset representing each of the plurality of patients is created by a computer. The dataset includes (x,y) pairs for each patient, wherein x is the type of medical data at the first time, and wherein y is the outcome measurement at the second time.

In step 130, the (x,y) pairs are ordered by a computer. In step 140, the (x,y) pairs are binned by a computer to form a plurality of binned data sets. In an embodiment, the bin size for each of the binned data sets is selected to have at least 2% of the total number of (x,y) pairs. In an embodiment, the (x,y) pairs are binned based on the values of x. In step 150, an average value for x (x_bar value) and an average value for y (y_bar value) for each binned data set is computed by a computer. In an embodiment, the dataset has enough (x,y) pairs so that each bin size has a sufficient number of (x,y) pairs so that the average value for x (x_bar value) and the average value for y (y_bar value) are statistically significant. In an embodiment, the dataset has number pairs (x,y) that span the values of x which are of interest. Given that the majority of values of x will be close to the average value for x (x_bar value), and given that the impact of deviations from the average are generally of great interest, the dataset should be large, on the order of thousands of points. In step 160, the minimum average value of y_bar (y_bar (min)) is subtracted from each y_bar value, resulting in a new average value for y_bar for each binned data set. In an embodiment, when y_bar (min) is subtracted from each y_bar value, a new value of y_bar (min) is zero. In step 170, a specific function y=f(x) for assessing risk associated with medical data is derived. In an embodiment, the function y=f(x) defines the excess risk due to deviation from normative values for the medical data. In an embodiment, if the type of medical data that is collected from an EMR is a continuous variable or an ordinal score, the specific function y=f(x) is a sum of a first function defined from average minimum value of x to average maximum value of x, a second constant function that covers values of x less than x_bar (min), and a third constant function that covers values of x greater than x_bar (max). In an embodiment, if a value for x is greater then x_bar (max) then the value of y is the value of y_bar that corresponds to the value of x_bar (max), and if a value for x is less then x_bar (min) then the value of y is the value of y_bar which corresponds to the value of x_bar (min). In an embodiment, the first function is derived by curve fitting through the (x_bar value, new y_bar value) points, to provide smooth interpolation between all of the x_bar values and all of the new y_bar values. In an embodiment, the curve is not used to extrapolate beyond the highest or lowest values of x_bar. In an embodiment, the first function is derived by fitting an appropriate functional form. In an embodiment, the functional form is selected from the group consisting of a line, a parabola, a polynomial, a sine function, and an exponential function. In an embodiment, the first function is derived by fitting a higher order polynomial derived using a linear least squares method. The curve represents the first function defined from average minimum value of x to average maximum value of x. In an embodiment, the curve that is fit through the points is well-behaved, that is, the curve smoothly interpolates between all of the x_bar values and all of the new y_bar values. In an embodiment, if the type of data that is collected is a categorical class or a binary assessment, the function y=f(x) is if x="a" then y=y_bar value for just value "a". In an embodiment, the function is used in computing a Health Score for a patient. In an embodiment, the function is used when lab results are reported to a physician, to give him/her a sense of, on average, what is the implication of a particular value of the medical data. In an embodiment, the function is used to help researchers better understand physiology.

In some embodiments, it may be desirable to create a two-dimensional array from the binned data sets by associating the x_bar value for each binned data set with one axis of the two-dimensional array and associating the corresponding new y_bar value for each binned data set with a second axis of the two-dimensional array.

In an embodiment, the type of medical data that is collected is a continuous variable. Examples of continuous variables include, but are not limited to, medical data obtained from a blood chemistry panel screen, medical data relating to an arterial blood gas (ABG) test, medical data relating to a blood analysis test, and medical data measuring a vital sign value. In an embodiment, the blood chemistry panel screen includes medical data relating to an albumin/globulin (A/G) ratio, an alanine aminotransferase (ALT or SGPT) value, an aspartate aminotransferase (AST or SGOT) value, an albumin value, an alkaline phosphatase value, a blood urea nitrogen (BUN) value, a calcium value, a carbon dioxide ($CO_2$) value, a chloride value, a creatinine value, a globulin value, a glucose value, a potassium value, a sodium value, a total bilirubin value, a total protein value and a tropon value. In an embodiment, the arterial blood gas test includes medical data relating to a base excess value, a fraction of inspired oxygen ($FiO_2$) value, a bicarbonate ($HCO_3$) value, a partial pressure of carbon dioxide ($PCO_2$) value, a partial pressure of oxygen ($PO_2$) value and a pH value. In an embodiment, the blood analysis test includes medical data relating to a hematocrit percentage, a hemoglobin value and a white blood cell count. In an embodiment, the vital sign value includes medical data relating to a heart rate value, a diastolic blood pressure value, a systolic blood pressure value, a respiration rate, a percentage of arterial hemoglobin in the oxyhemoglobin configuration (pulse Ox) and a temperature value. In an embodiment, the type of medical data that is collected is an ordinal score, such as a Braden scale score.

Figure 2:
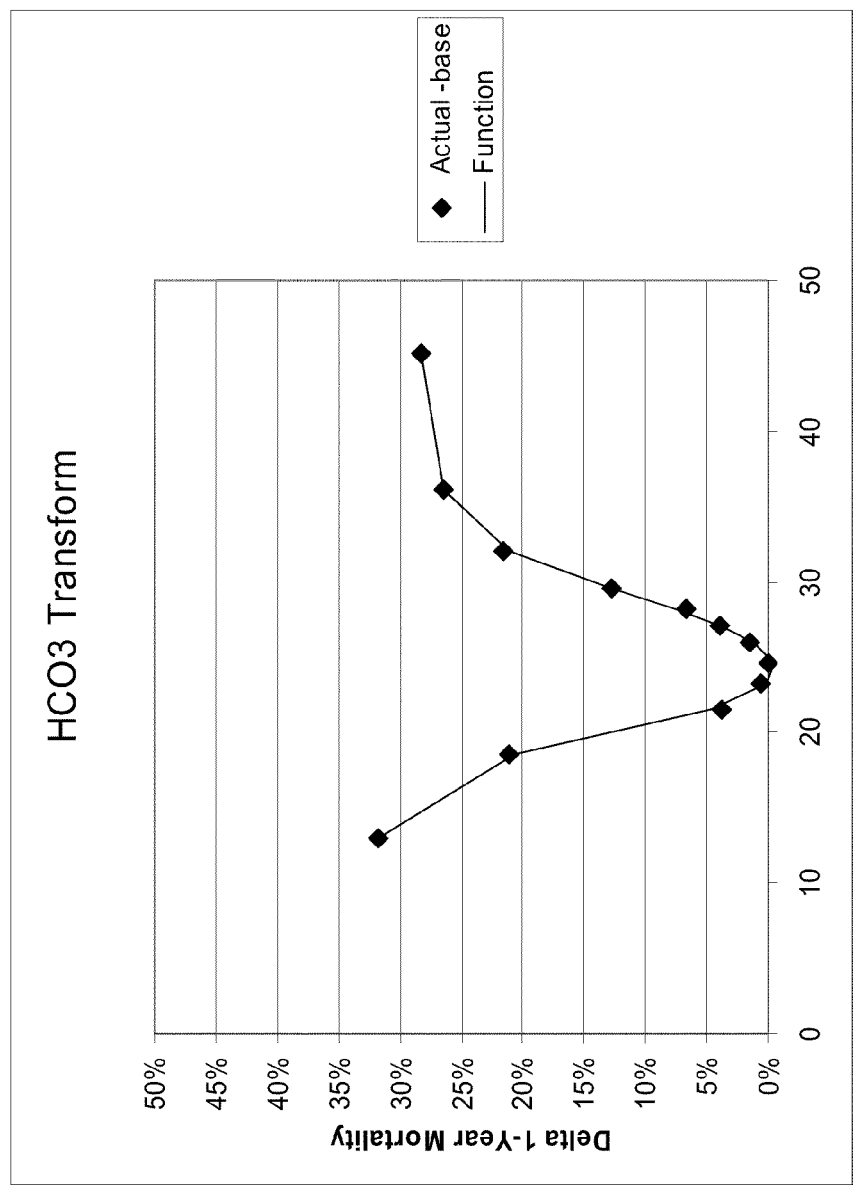
FIG. 2 is a graph of an excess risk curve where an outcome measurement (mortality 1-year post discharge-base) is a function of bicarbonate ($HCO_3$) at discharge.

FIG. 2 is a graph of an excess risk curve where an outcome measurement (mortality 1-year post discharge-base) is a function of a continuous variable (bicarbonate) at discharge. The medical data was obtained from EMR data from about 22,000 patients. Using the method steps of FIG. 1, a $6^{th}$ order polynomial defining the excess risk due to deviation from normative values for bicarbonate was derived. The excess risk curve shows that a bicarbonate value of approximately 24 mEq/L (conventionally considered a "normal value") results in a 0% excess risk for a patient, however a bicarbonate value of approximately 13 mEq/L (conventionally considered a "low value") results in an about 33% excess risk for a patient.

Figure 3:
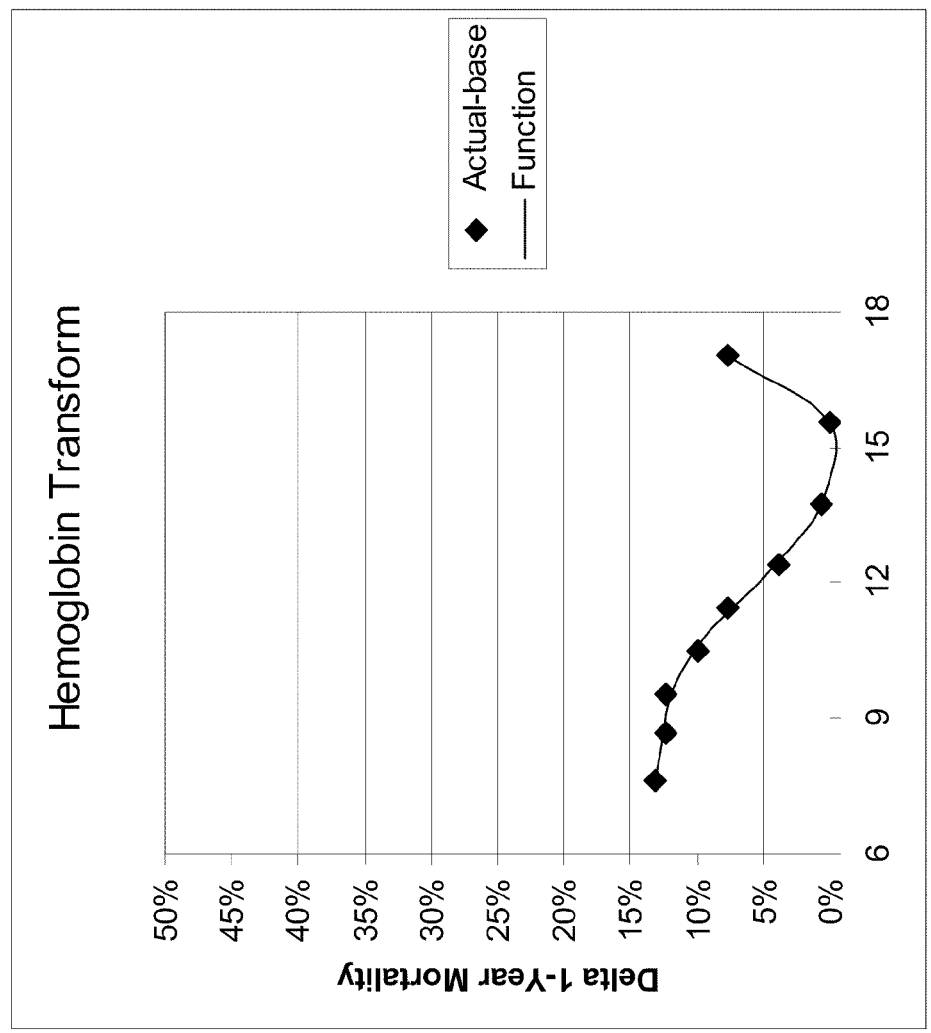
FIG. 3 is a graph of an excess risk curve where an outcome measurement (mortality 1-year post discharge-base) is a function of hemoglobin at discharge.

FIG. 3 is a graph of an excess risk curve where an outcome measurement (mortality 1-year post discharge-base) is a function of a continuous variable (hemoglobin) at discharge. The medical data was obtained from EMR data from about 22,000 patients. Table 1 shows x_bar values (i.e., Avg. Hgb) and new y_bar values (i.e., Avg. 1-year mortality-Base) for nine binned data sets each binned data set with N number of patients. A $6^{th}$ order polynomial defining the excess risk due to deviation from normative values for bicarbonate was derived. The excess risk curve shows that a hemoglobin value of approximately 15.5 gm/dL (conventionally considered a "normal value") results in a 0% excess risk for a patient, however a hemoglobin value of approximately 7.64 gm/dL (conventionally considered a "low value") results in an about 13.1% excess risk for a patient.

TABLE 1

| N | Avg. Hgb | Avg. 1-year mortality | Avg. 1-year mortality-Base | Bin Range |
|---|---|---|---|---|
| 307 | 7.65 | 0.23 | 0.13 | 2-8.3 |
| 545 | 8.66 | 0.22 | 0.12 | 8.3-9 |
| 2473 | 9.51 | 0.22 | 0.12 | 9-10 |
| 4081 | 10.47 | 0.20 | 0.10 | 10-11 |
| 3979 | 11.44 | 0.17 | 0.08 | 11-12 |
| 3270 | 12.42 | 0.14 | 0.04 | 12-13 |
| 3618 | 13.77 | 0.10 | 0.01 | 13-15 |
| 673 | 15.55 | 0.10 | 0.00 | 15-16.5 |
| 150 | 17.05 | 0.17 | 0.08 | 16.5-21 |

Figure 4:
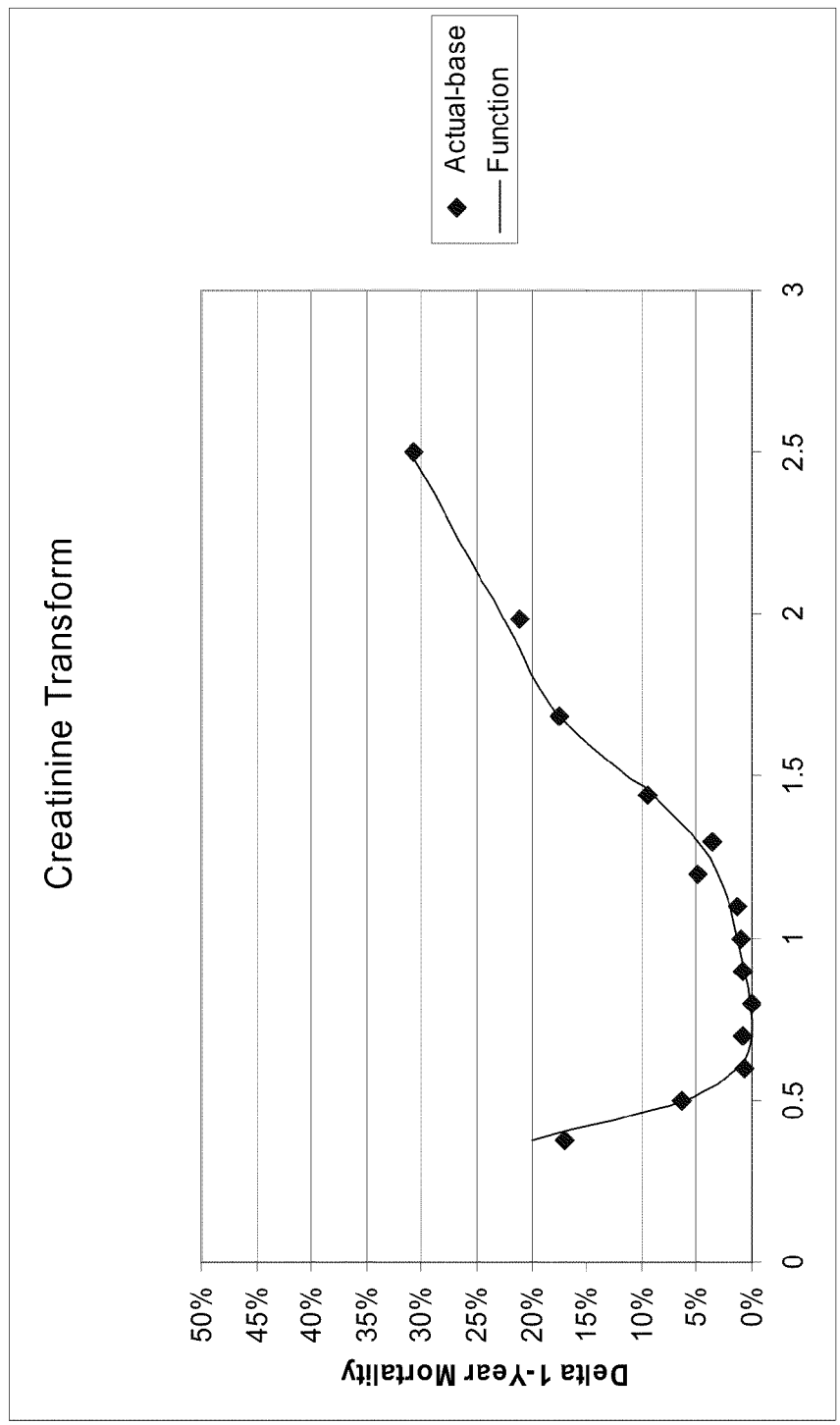
FIG. 4 is a graph of an excess risk curve where an outcome measurement (mortality 1-year post discharge-base) is a function of creatinine at discharge.

FIG. 4 is a graph of an excess risk curve where an outcome measurement (mortality 1-year post discharge-base) is a function of a continuous variable (creatinine) at discharge. The medical data was obtained from EMR data from about 22,000 patients. A $6^{th}$ order polynomial (fit in the range of 0.37 mg/dL to 2.5 mg/dL) defining the excess risk due to deviation from normative values for bicarbonate was derived. The excess risk curve shows that a creatinine value of approximately 0.8 mg/dL conventionally considered a "normal value") results in a 0% excess risk for a patient, a creatinine value of approximately 2.5 mg/dL (conventionally considered a "high value") results in an about 31% excess risk for a patient, and a creatinine value of approximately 0.37 mg/dL (conventionally considered a "low value") results in an about 17% excess risk for a patient. If a creatinine value for a different patient is less then 0.37 mg/dL, then delta-one year mortality will be equal to 20%. If a creatinine value for a different patient is more then 2.5 mg/dL, then delta-one year mortality will be equal to 30%.

Figure 5:
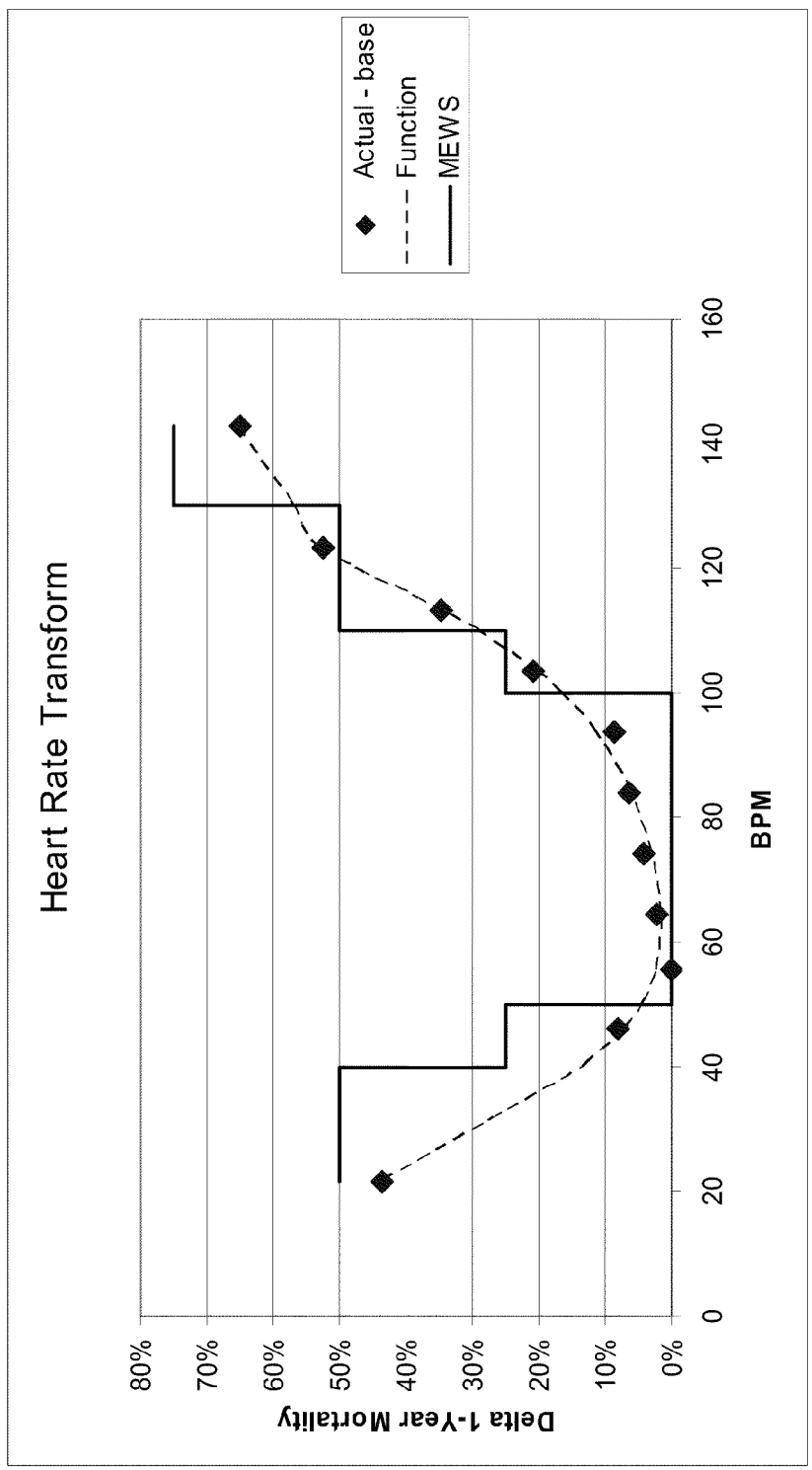
FIG. 5 is a graph of an excess risk curve where an outcome measurement (mortality 1-year post discharge-base) is a function of heart rate at discharge.

FIG. 5 is a graph of an excess risk curve where an outcome measurement (mortality 1-year post discharge-base) is a function of a continuous variable (heart rate) at discharge. The medical data was obtained from EMR data from about 22,000 patients. A $6^{th}$ order polynomial defining the excess risk due to deviation from normative values for bicarbonate was derived. The excess risk curve shows that a heart rate value of approximately 55 BPM (conventionally considered in the range of "well-trained athletes") results in a 0% excess risk for a patient, however a heart rate value of approximately 92 BPM (conventionally considered in the high range of a "normal value") results in an about 9% excess risk for a patient. Also shown in FIG. 5 is a Modified Early Warning System (MEWS) curve for heart rate which identifies people at risk of deterioration in a busy ward. The MEWS curve contains a risk transform in the form of a step function: output=2 if HR<40, output=1 if HR is between 40 and 50, output=0 if HR is between 51 and 100, output=1 if HR is between 100 and 110, output=2 if HR is between 110 and 130, and output=3 if HR is greater then 130. The step function is plotted by setting 1 point=25%. As illustrated graphically in FIG. 5, there is a correspondence between the two transformation curves (MEWS) and the excess risk curve of the function. These are derived completely independently. The MEWS step-function curve comes from the accumulated observations of experts in the field, doctors having witnessed many patients go through crises.

Figure 6:
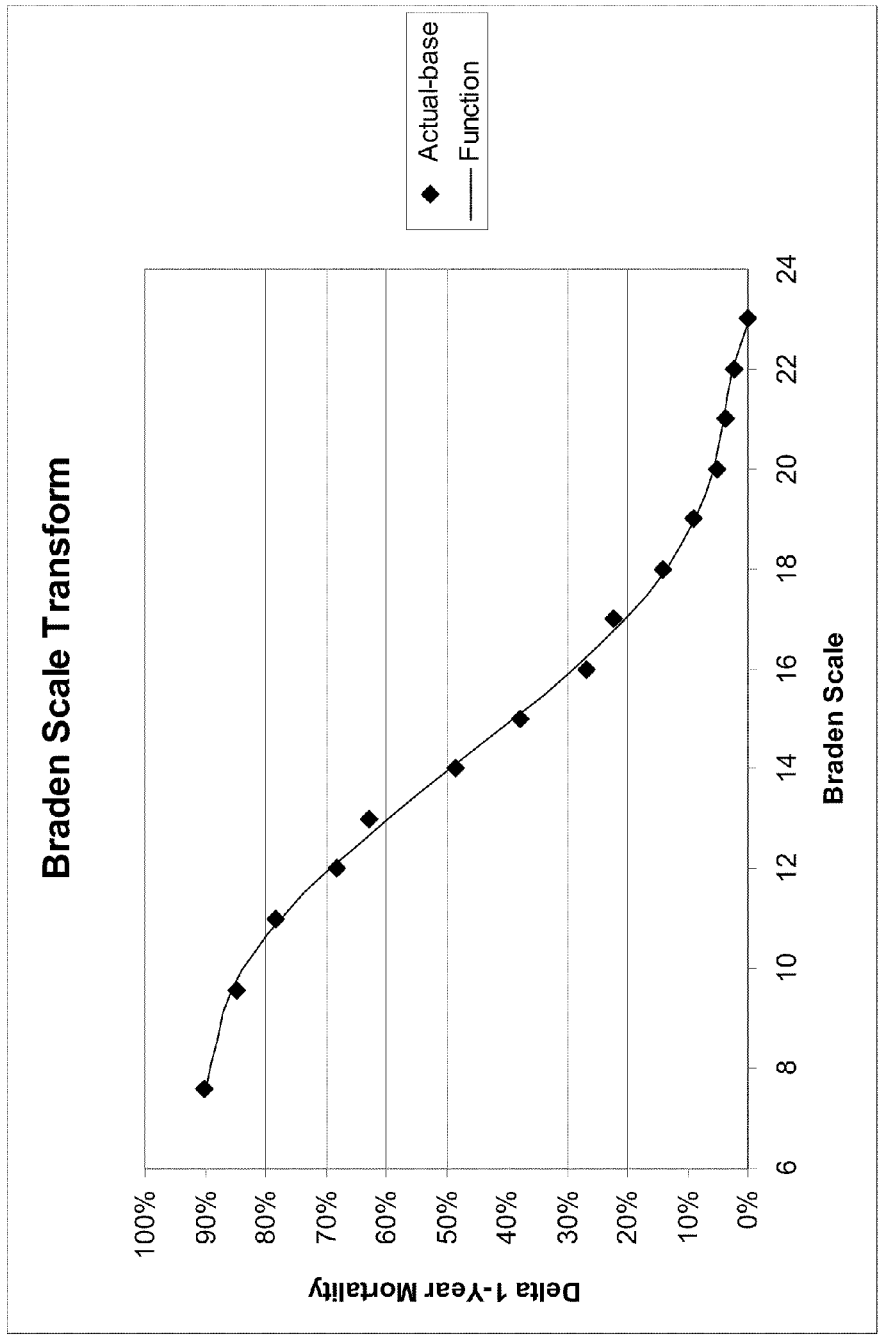
FIG. 6 is a graph of an excess risk curve where an outcome measurement (mortality 1-year post discharge-base) is a function of Braden Scale at discharge.

FIG. 6 is a graph of an excess risk curve where an outcome measurement (mortality 1-year post discharge-base) is a function of an ordinal score (Braden Scale) at discharge. Medical data used to derive the function was obtained from EMR data from about 22,000 patients. Points on the graph are average one-year mortality for a given Braden scale score less base mortality for a Braden score of 23 (base mortality is 2.6% for a Braden score of 23). Average one-year mortality versus average Braden scale score for distinct ranges were fit to a $5^{th}$ order polynomial.

In an embodiment, the type of medical data that is collected is a categorical class. An example of a categorical class includes, but is not limited to, a heart rhythm distinction. In an embodiment, the heart rhythm distinction includes sinus bradycardia, sinus rhythm, heart block, paced, atrial fibrillation, atrial flutter, sinus tachycardia and junctional rhythm. In an embodiment, the type of medical data that is collected is a binary assessment. An example of a binary assessment is subjective data, such as nursing assessments. In an embodiment, the binary assessment is a nursing assessment. In an embodiment, the variable selected from the nursing assessment includes, but is not limited to, a food assessment, a neurological assessment, a psychiatric assessment, a safety assessment, a skin assessment, a genitourinary assessment, a muscular-skeletal assessment, a respiratory assessment, a cardiac assessment, a peripheral vascular assessment, a gastrointestinal assessment, a Braden scale assessment and a pain assessment.

Figure 7:
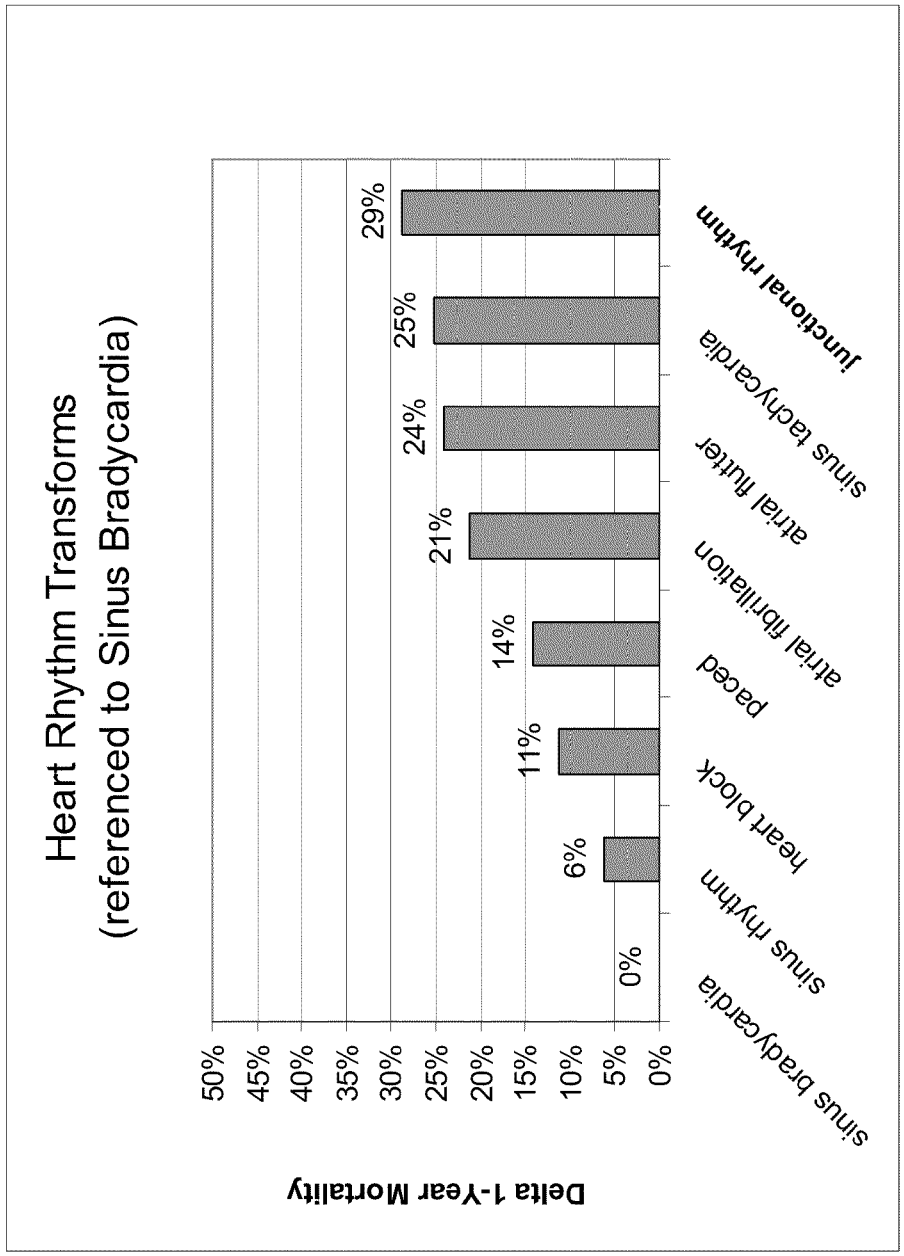
FIG. 7 is a graph of an excess risk curve where an outcome measurement (mortality 1-year post discharge-base) is a function of heart rhythm at discharge.

FIG. 7 is a graph of an excess risk curve where an outcome measurement (mortality 1-year post discharge-base) is a function of a categorical class (heart rhythm distinction) at discharge. The medical data was obtained from EMR data from about 22,000 patients. The excess risk curve shows that a heart rhythm of sinus bradycardia (conventionally defined as a heart rate of under 60 BPM) results in a 0% excess risk for a patient. A heart rhythm of atrial fibrillation (conventionally defined by the quivering of the heart muscles of the atria) results in an 21% excess risk for a patient. A heart rhythm of junctional rhythm results in a 29% excess risk for a patient.

Figure 8:
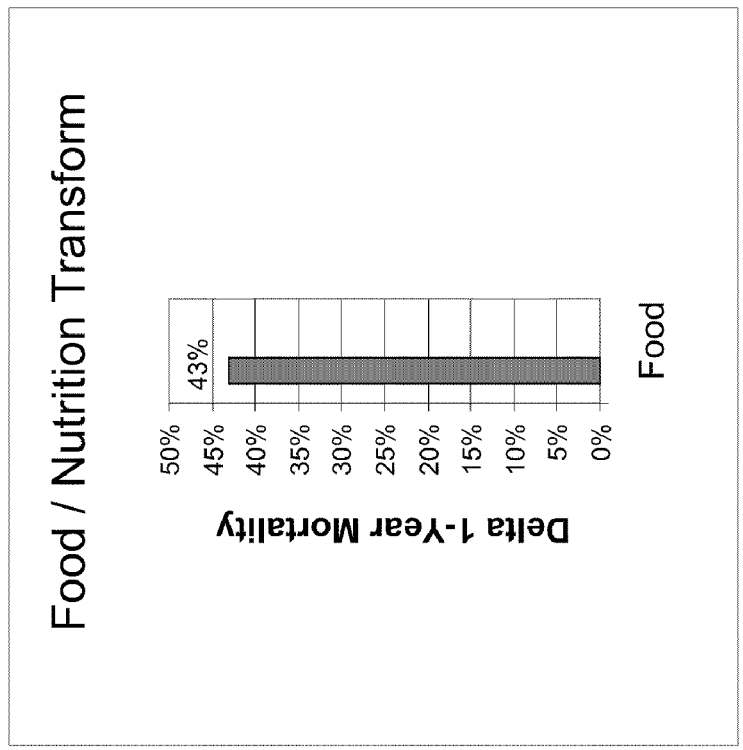
FIG. 8 is a graph of an excess risk curve where an outcome measurement (mortality 1-year post discharge-base) is a function of a food/nutrition assessment at discharge.

FIG. 8 is a graph of an excess risk curve where an outcome measurement (mortality 1-year post discharge-base) is a function of a binary assessment (food/nutrition nursing assessment) at discharge. Medical data used to derive the function was obtained from EMR data from about 22,000 patients. The excess risk curve shows that if a patient has failed a food/nutrition nursing assessment, there is a 43% excess risk for a patient.

It should be understood that although the embodiments described in FIGS. 1-8 describe the deriving of a function based on a single independent variable (type of medical data), the methods disclosed herein are also applicable for deriving functions based on two or more independent variables (types of medical data). As with functions of one variable, functions of several variables can be represented numerically (using a table of values), algebraically (using a formula), and sometimes graphically (using a graph).

In an embodiment, a general measure of risk for a hospitalized patient, sensitive to the full range of patient conditions, available for use throughout a hospital, independent of diagnosis, is developed which can be used to assess a patient's state, and more particularly to system and methods for recognizing downtrends which may indicate the onset of a complication. Embodiments of the present disclosure provide system and methods for recognizing downtrends in a patient's health, which may indicate the onset of a complication, and to aid in communication of this information across staff handoffs. At least some of the embodiments allow for continually tracking the health of a patient in a hospital. At least some of the embodiments allow physicians, nurses and clinical researchers to provide more effective health care for each patient, especially those spending several days in a hospital. In addition or alternatively, at least some embodiments assist hospitals in avoiding errors and reducing crisis management by using the systems' capability to detect trends in a patient's health before the patient reaches a crisis point. Recognizing a decline soon enough to administer proper treatment may be a life-saving benefit. Embodiments of the system may give physicians and nurses a way in which to get the "big picture" of a patient's condition and absorb in a glance perhaps 100 pages of a patient's medical records. This deeper understanding, along with this new capability to detect health trends, short-term (over the space of hours) and/or long-term (over the space of days) may be important in delivery of effective medical care. Embodiments may enable a new field of scientific study, where medical and surgical treatments can be evaluated by the new measurements provided by embodiments of the present disclosure.

Embodiments of the present disclosure generate a new measurement of health, herein termed the patient "Health Score," which may be continually plotted and displayed to show each patient's medical progress during his hospital stay. The health of the patient may relate a patient's vitality and overall quality of life rather than simply being free from disease. Although a patient who has a terminal disease, such as cancer, may conventionally be considered to be in 'poor health'; however, if a cancer patient who only has a few months to live is playing ping pong for hours, he/she may be considered to be in good health, as the term is used herein. In comparison, a patient who entered the hospital to have a simple surgery, such as a tonsillectomy, may conventionally have been considered to be and will likely recover to be in 'excellent health.' However, while recovering, the tonsillectomy patient's vitality might be low and his/her change of dying in the near future could be much higher if a complication were to arise; thus, the patient may be considered to be in poor health, as the term is used herein. The health of a patient may relate to the patient's overall physical, mental, spiritual and social wellbeing and not merely the absence of disease or infirmity. Embodiments of the present invention may prove to be a vital aid for improving the quality and continuity of medical care.

To this end, embodiments of the present invention may provide systems for improving hospital patient care by generating a Health Score. The system may include an interface module for receiving incoming medical data from a patient, a transformation module for transforming the medical datum into a transformed Health Score value, and a combination module for combining the transformed Health Score values corresponding to each of the medical datum into a single Health Score. A presentation and/or comparison module displays the Health Score as a Health Score plot over a predetermined time frame, such that a user may identify health trends in a patient by evaluating said Health Score plot. The Health Score system is described in more detail below.

In addition to the features of the Heath Score and uses thereof, it is further contemplated that an exemplary use of such system may include the use of the Health Score to provide a panel of Health Score Charts, giving a nurse or doctor an overview as to the progress of many patients at one time, as is described further below.

In one embodiment, the Health Score may be used to predict the odds of a crisis within N number of hours. That is, for example, there is a 20% chance of a crisis in the next 12 hours. This information may be used to assign additional observation to particular patients, or if a crisis is judged to be imminent, a call may be initiated to a Rapid Response Team. Another use for the Health Score is to route doctor's rounds, so that walking instructions can be provided for a doctor doing rounds. This will allow a doctor to quickly move to patients requiring more attention first, and then proceed to less critical patients. A doctor or nurse may annotate a chart, such as adding a comment, for example "Breathing well," or a nurse could say "Tubes removed." Charts may also be annotated by adding special ICONS . . . for example, a walking man to show that the patient is now mobile. The name of the doctor who is treating the patient may also be added to the chart.

One way in which a crisis may be predicted is by comparing the individual patient's Health Score with a standard recovery curve. By tailoring the standard recovery curve to the patient, better results may be obtained. For example, one of the exemplary ways in which patients may be categorized is by DRG/ICD-9 grouping systems. DRG stands for a diagnostic related group and ICD-9 is the international classification of disease. Both of these are ways of categorizing patients based on what disease or ailment the patients have and are employed by insurance companies to figure out how much the insurance company should pay out for a particular policyholder in the hospital. For example, the standard recovery curve for someone having had elective rhinoplasty is likely to be very different from the standard recovery curve of someone who had a heart-lung transplant. If the rhinoplasty patient's health was declining, but the rhinoplasty patient's health was viewed in comparison with someone who had serious surgery, such as a heart-lung transplant, the decline might not be viewed as being significant, while in reality the rhinoplasty patient could be about to experience a cardiac or respiratory crisis. If the transplant patient's health is improving, but the patient's health is viewed in comparison with other patients who have had the same procedure and the recovery is much slower this could be an early indication of a complication. By comparing patients based on their disease, treatment/surgery, or affliction, the patient's Health Score may be better interpreted.

In some embodiments, ICD-9, which groups patients into thousands of detailed categories, normative data plots may be used, while in some embodiments DRG, which groups patients into about 500 categories, may be used, while in yet other embodiments, a combination of the two grouping systems may be used. Not all embodiments are intended to be limited in this respect and any disease grouping system or data may be employed to create a singular or combination standard recovery curve.

In some embodiments, creating the standard curve may entail reviewing graphs of all previous patients with the same DRG/IDC-9 code in a database and plotting them as one or more curves. The curve may be represented by an average curve, all of the individual patient's curves, a median curve, a top $25^{th}$ percentile and a bottom $25^{th}$ percentile, plus or minus some number of standard deviations thereby creating a normative recovery as well as upper and lower bounds, any combination of the foregoing or any other representative indicator as not all embodiments of the present disclosure are intended to be limited in this respect. By using these types of normative curves a doctor may be able to see that even if a patient is recovering, the patient might be recovering more slowly (too shallow a slope) than the average patient with a similar condition and this slower recovery might be cause for further investigation.

Not only may the grouping codes be useful in comparison with the Health Score, but the grouping codes may be utilized in generating a more accurate Health Score. In some embodiments, a user may modify the algorithm used to generate the Health Score based on the diagnosis or grouping code of the patient in order to have the Health Score more accurately reflect the patient's recovery Yet another exemplary use of the Heath Score arrangement is its use in predicting the length of stay for a patient or group of patients, sometimes termed ELOS (expected length of stay). Such an arrangement may be used to apply to a group of patients and therefore allowing a hospital to create a forward-looking resource plan, i.e. how many nurses are needed on a subsequent day of the week based on the current hospital population in a particular department. Some grouping codes, such as DRG, have ELOS times built into the grouping code, such that someone having a certain surgery will have an ELOS of a certain amount of time. For example, a patient having knee surgery may have an ELOS of 2.3 days and the hospital will be paid accordingly. However, if the patient actually takes 4.1 days to recover, the hospital may lose money or the patient may have to pay the difference, but if the patient if discharged after 1.5 days, the hospital may earn a profit.

In some embodiments, the life expectancy or mortality of a patient, such as the likelihood that a patient will die within the next 24 hours, may be predicted. For example, if a terminal patient is listed as DNR (do not resuscitate) or "keep patient comfortable," a family member may want to know the life expectancy of the terminal patient to plan for the inevitable death.

By comparing a patient's Health Score with a standard, many inferences may be drawn from the comparison. For example, in some embodiments, patients may be given a category, such as critical, critical but stable, serious, serious but stable, fair, and/or good. These categories may be words or terms, numbers (such as 1-5 or 1-100), colors (such as red, orange, yellow, or green), a made up system of categorizing, or any other system. In addition, the categories may be discrete, such as choosing one of four colors or may be continuous, such as choosing any number from one to 100.

By having patients categorized, administrative decisions and care priority can be determined accordingly. For example, in some embodiments, a nurse scheduling tool may be incorporated or separately determined which would allow shift nurses to see the conditions of all patients on the floor and assign nurses based on skill level, so that more experienced nurses have more critical patients and newer nurses have more stable patients. In some embodiments, the nurse scheduling tool may rank patients, for example, 1-10 and allocate patients to each nurse so that no nurse has a total patient rank of for example, more than 25 (e.g., two very critical patients of rank 10 and one fair but stable patient of rank 5, four fair but stable patients of ranks 5.2, 5.4, 5.7 and 6.1, or two serious patients of rank 8 and one serious but stable patient of rank 7.2). In some embodiments, the ELOS prediction may be incorporated into the nursing schedules, so that discharges may be predicted and the charge nurse may be able to know how many staff members may be required to work an upcoming shift. Similarly, these systems may be applied to routing a doctor's rounds, as described above.

In another possible arrangement, the Health Score may be used to determine priority and timing of the post-discharge "how are you doing" call. For example, patients leaving the hospital with favorable Heath Scores may be called in three days for a checkup, whereas patients with marginally acceptable Heath Scores may be called sooner.

The Heath Score as disclosed in the incorporated documents, and above may be fine tuned to each hospital in which it is implemented. Most hospitals have slight differences in procedures, standards, requirements and other elements of daily practice as compared to other hospitals and some embodiments of the present disclosure may be adapted to a specific hospital's preferences. In particular, when using subjective variables to produce a Health Score, as will be described further below, some hospitals may be more conservative in evaluating a patient's condition. For example, nurses at a first hospital may be taught that slightly grey skin is a reason to fail a skin assessment while nurses at a second hospital may be taught that a patient should pass a skin assessment until the skin is really grey. This difference may make average scores on the Health Score lower at the first hospital, which could mean that the predicted health of a patient would appear worse at the first hospital than at the second hospital. By adjusting the Health Score according to an individual hospital's procedures, the Health Score may be more accurate.

In some embodiments, the Heath Score may be used for evaluation purposes. For example, the Heath Score may be used to evaluate the performance of a particular doctor's or nurse's performance, or even of the hospital itself. It can also be used to evaluate a particular treatment by studying Heath Score charts of patients that underwent a particular treatment.

In addition to evaluation of doctors, the system may be used to compare effectiveness of medical treatments, compare the quality of care provided by different wards or hospitals, and compare the skill of healthcare providers by providing an objective assessment of a patient's health and response to various factors. In some embodiments, the algorithm may be customized after a patient's stay to further evaluate the care of the patient and compare the patient with other patients. For example, if two patients had the same diagnosis and received different treatments, a hospital or doctor may want to compare those two patients' recoveries. However, if one patient had a small drop in their Health Score due to an unrelated event, such as having an allergic reaction to topically applied medication, the algorithm may be adjusted to exclude a factor, such as a skin standard of the nursing assessment, from the Health Score of both patients, so that the two patients are still evaluated using the same algorithm, but the comparison is tailored to focus on the recovery from the treatments and exclude unrelated deviations.

In another embodiment, the Health Score chart shapes can be clustered to discover the "types" of patient health trajectories. General prototypical trajectories, or trajectories computed as a function of disease or procedure may be compared against actual Heath Score charts to determine how a particular patient is responding to treatment. Once a Health Score chart is assigned to such a prototypical trajectory, it may further indicate the likelihood of various outcomes. In some embodiments, this may be accomplished by using DRG/IRC-9 groupings, as discussed herein.

In another embodiment of the present disclosure, the Heath Score may be used as part of a remote monitoring service, where a remote health service provider can monitor the score of several patients and alert an on-site staff if there is an emergency. The Health Score can be refined using neural networks, or other analytical methods. The Health Score may be fed to a central data hub and be used to monitor for large scale trends in health problems, including a biological or chemical attack.

While in some embodiments an individual Health Score falling below a minimum mark or the change in Health Score or slope of the Health Scores falling below a minimum change may trigger an alarm or be interpreted by a healthcare provider as an indication of the patient's declining health, in some embodiments the change in slope or derivative of the slope of the Health Scores falling below a certain minimum may trigger an alarm or be interpreted by a healthcare provider as an indication of the patient's rapidly declining health. For example, if a patient is slightly declining and suddenly starts to decline at a much faster rate, this change in the acceleration of the slope may trigger an alarm. In some embodiments, the curvature of the Health Score plot may be provided, such as by a presentation and/or comparison module.

Many times a patient's health may be compromised in favor of conforming the patient's care to hospital standards. For example, many hospitals require their healthcare workers to take a patient's vital signs every 2-4 hours, which requires awakening patients during the night and often times not allowing them to complete a full sleep and enter deep sleep, which may be critical to a patient's recovery, and to draw blood from patients every day or two, which can be detrimental to an anemic or hemophiliac. If a patient has been recovering well and has an increasing Health Score, a healthcare worker may rely on the Health Score to determine whether or not a routine test or procedure may be skipped in order to allow the patient to better recover.

The system may include the ability to view a patient's prior hospital visits. In some embodiments, if a patient has a recurring condition, it may be preferable to view that patient's past Health Scores in addition to the present Health Score. In addition or alternatively, the graph may display a one or more Health Scores calculated using different inputs, such as a red line with circular data points for when the entry reflects nursing assessments, a blue line with square data points for blood work and/or a green line with triangular points for a chem panel. Differences in data source may be represented with unique icons or any other means of differentiating them, as not all embodiments are intended to be limited in these respects. In addition or alternatively, a doctor or healthcare provider may click on or hover over a point to access additional information, such as the data inputted to calculate the Health Score, an average reading, values from earlier in the patient's stay, or any other information.

In some embodiments of the present disclosure, a Health Score system is provided for generating and presenting a Health Score chart. The Health Score may be a medical reference "figure-of-merit" that is used by a health caretaker, such as a physician, nurse or other health attendant, to track the patient's health before, during or after a medical procedure or illness, in order to assist in preventing that patient from reaching a health crisis. When used in this manner, the Health Score chart enables the attending physicians and nurses to detect trends in the patient's health over time, particularly in evaluating post-operative recovery in the hospital. The Health Score chart also provides a statistically significant "outcome" for both clinical studies and retrospective studies of the relative efficacies among various surgical procedures or techniques, and among medical treatments and drugs.

In addition to short term intensive use of the Health Score system, a similar modified form may be used on a long term basis by regular general practitioners or other health care facilitates such as nursing homes. For example, as it stands, yearly physicals are usually accompanied by a series of medial measurements of the patient. Entering such data in Health Score system may be useful in spotting long term declining health trends, even if none of the particular medical conditions have reached a crisis level.

Figure 9:
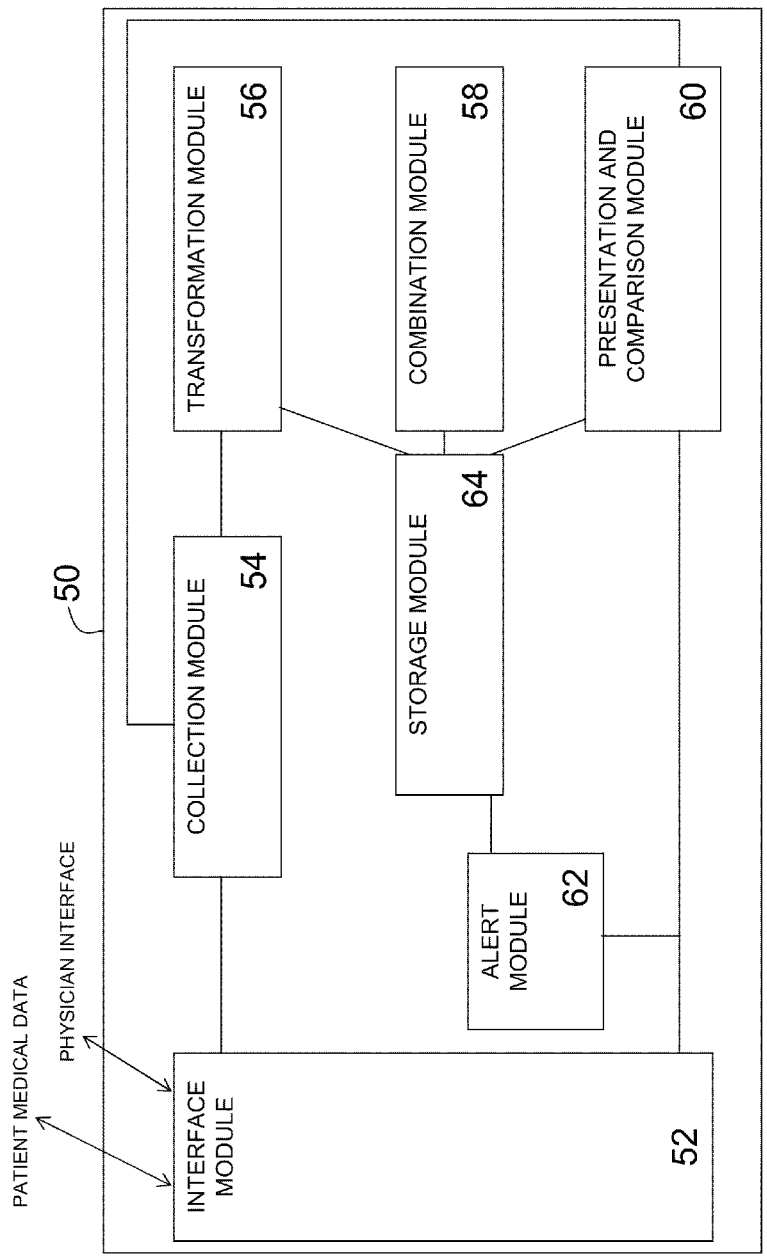
FIG. 9 depicts a logical diagram of an embodiment of a Health Score system of the present disclosure.

To generate and present the Health Score, as illustrated in FIG. 9, Health Score system 50 may have an interface module 52, a collection module 54, a transformation module 56, a combination module 58, a presentation and/or comparison module 60, an alert module 62, and/or a storage module 64. A computer or computing device such as system 50 includes a processor and memory for storing and executing program code, data and software modules which may be tangibly stored or read from any type or variety of well known computer readable storage media such as magnetic or optical discs, by way of non-limiting example. System 50 can be provided with operating systems that allow the execution of software applications in order to manipulate data. Personal computers, personal digital assistants (PDAs), wireless devices, cellular telephones, internet appliances, media players, home theater systems, servers, and media centers are several non-limiting examples of computing devices.

Interface module 52 is configured to obtain or receive raw medical data, either directly from patient monitoring devices, or from attending physicians or nurses. Collection module 54 collects the raw medical data from interface module 52, and further may collect additional material from storage module 64, including the patient's historical medical data as well as other required general medical data (optional statistics) In some embodiments, the raw medical data may be transmitted to transformation module 56, and the stored and historical medical data may be sent to presentation and/or comparison module 60. In some embodiments, the medical and historical data may be sent to the transformation module 56 and/or the presentation and/or comparison module 60.

Transformation module 56 receives incoming raw medical data and converts (transforms) each of the data into a usable format for generating the patient's Health Score. Transformation module 56 converts each of the raw medical data into a form that will allow different types of data to be combined, such as a scaled number. These converted raw medical data are referred to as Health Score values. In an embodiment, the transformation module 56 converts raw medical data into scaled numbers based on the derived functions, as was described above in FIGS. 1-8. In an embodiment, the functions are stored in the memory of system 50. In an embodiment, the functions are stored in the memory of a separate computer or computing device that is in communication with system 50. In an embodiment, the transformation module 56 converts each of the incoming raw medical data by plugging in the value of the raw medical data into the excess risk function that was derived as described in FIG. 1. In an embodiment, the transformation module 56 takes a past value of one type of raw medical data, compares it with a current value of the same type of raw medical data, determines the change in the raw medical data value, and uses the change in value as the input to the excess risk function. In an embodiment, the transformation module 56 takes past values of one type of raw medical data, adds it to a current value of the same type of raw medical data, determines the average value for the raw medical data, and uses the average value as the input to the excess risk function.

As an illustrative example, if the raw medical data collected from the patient is a hemoglobin (Hgb) value corresponding to 10.47 gm/dL, the Health Score value can be determined by plugging the value of 10.47 gm/dL into the $6^{th}$ order polynomial function, which represents excess risk due to deviation from normative values, as a function of hemoglobin measured against one-year mortality. This would result in a Health Score value for hemoglobin of approximately 10%. Therefore, the transformation module 56 would convert the Hgb value of 10.47 gm/dL to a transformed Health score value of 10%. Similarly, if the raw medical data collected from the patient is a creatinine value corresponding to 2.5 mg/dL, the Health Score value can be determined by plugging the value of 2.5 mg/dL into the $6^{th}$ order polynomial function, which represents excess risk due to deviation from normative values, as a function of creatinine measured against one-year mortality. This would result in a Health Score value of approximately 31%. Therefore, the transformation module 56 would convert the creatinine value of 2.5 mg/dL to a transformed Health score value of 31%.

The transformed data may then be sent to combination module 58, which in turn may generate a patient's Health Score, using a predetermined algorithm. In an embodiment, the combination module 58 takes the sum of each of the single-variable risks. The combination module 58 may combine the transformed Health Score values and scale them, so that they span a given range. If a Health Score was defined so that a high value corresponded to "good health" and a low value corresponded to "poor health", then the scaled total transformed Health Score value would be subtracted from the "best" value of health. For example if the best value were 100, and the range was to be 100, that is poor health was to correspond to zero, then the scaled total transformed Health Score value would be subtracted from 100. If the scale factor was 0.1 and a Health Score was computed based just upon these two variables, the two Health Score variables would be combined (10+31=41) and then the quantity 41 times 0.1 (or 4.1) would be subtracted from 100 and come up with a Health Score of 95.9. Therefore, the combination module 58 would generate a Health Score for the patient to be 95.9 at that time. This example describes a Health Score determination based on two types of raw medical data. Typically, the Health Score would be determined based on 15, 20, 25, 30 or more types of raw medical data.

Presentation and/or comparison module 60 may receive the calculated Health Score and may prepare a Health Score chart, plotting the patient's Health Score as a function of time. In some embodiments, the presentation and/or comparison module 60 may display, using, for example, a screen or monitor, the Health Score as a Health Score chart over a predetermined time frame, such that a user may identify health trends in a patient by evaluating the Health Score chart. Alert module 62, may generate an alarm for the attending physicians and nurses when a problem is detected with a patient's Health Score chart. An alert may be activated for such problems when the Health Score of a patient descends below an acceptable threshold, determined in advance by system 50 or set by the attending physician, or if a downward trend is detected. Storage module 64 may be configured to store and retrieve Health Score information at various times during the Health Score generation and presentation procedure.

It is understood that the above list of modules is intended only as a sample of the logical organization of modules within system 50. For example, many of the modules may be combined with one another or subdivided and separated according to their function. In some embodiments, a data module may act as a collection for all data, both as inputted into an interface module and as stored in a storage module, a conversion module may transform and combine the data using an algorithm and creating an output, and a display module may present and compare the output as well as alert a healthcare provider to a potential issues. Any similar Health Score system, employing similar logical modules to obtain a Health Score is also within the contemplation of the present disclosure.

Furthermore, it is noted that the modules of system 50, illustrated in FIG. 9, are to show their logical relationship to one another. However, this is not intended to limit the physical construction of such a system. For example, system 50 may be employed on a single larger computer or on a series of smaller computers, possibly with different components residing within different geographical locations, such as the use of an off-site storage module 64. Any health care system 50 may employ similar modules to generate a Health Score alert, as not all embodiments of the present disclosure are intended to be limited in this manner.

Figure 10:
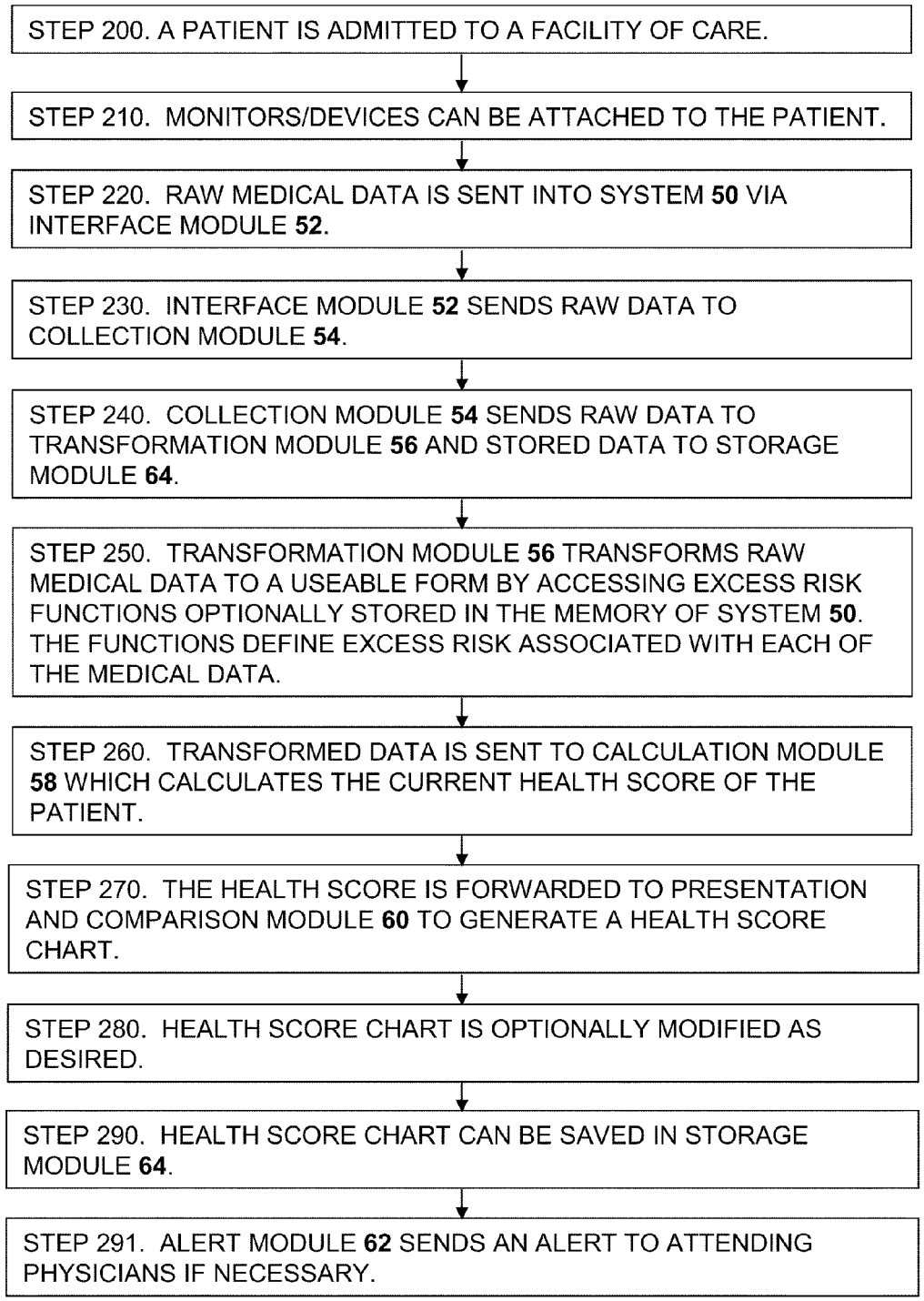
FIG. 10 is a flow chart showing an embodiment of a method of generating a Health Score chart.

FIG. 10 is a flow chart showing an embodiment of a method of determining an overall risk inherent in a patient's current condition. In step 200, a patient is admitted for a particular illness or surgical procedure. At step 210, the patient can be connected to various medical devices/monitors for obtaining at least some of the pertinent raw medical data, although this step is optional.

At step 220, interface module 52 begins obtaining the pertinent raw medical data about the patient and imports this data into system 50. Some data may be obtained directly from the attached medical devices or from electronic medical records. Other data may be entered into the system by an attending physician or nurse. Typically, the input may include any number of the medical statistics that are used to generate the Health Score produced by system 50. Interface module 52 of system 50 may be hardware, such as a keyboard and monitor, used for manual entry of patient data. Furthermore, interface module 52 may additionally include a set of automated electrical instruments such as pulse clips, automated blood pressure devices, blood oxygen measuring devices, fluid monitoring devices or any other standard medical measuring device, attached either by wire or remotely to interface module 52.

In addition to providing an interface for receiving medical data on the patients, interface module 52 may also be configured to present a means for users, such as doctors or nurses, to update, modify or review the patient's Health Score at step 280. Furthermore, interface module 52 may also be employed by alert module 62 at step 291 to alert the healthcare providers that alert module 62 has detected a threshold breach, which is explained in greater detail below At step 230, the data may be sent to collection module 54. Collection module 54 may be coupled to interface module 52 for receiving the various raw patient data at step 230. Collection module 54 may accept this data from various ports, including interface module 52 as well as other programs, such as electronic medical records (EMR), and stores this data in storage module 64. At step 240, collection module 54 may further obtain any necessary past medical data, most importantly the past Health Scores of the same patient. Thus, in addition to the raw physical patient data and physician/nurse input obtained from interface module 52, collection module 54 may further collect and organizes all of the data necessary to generate and maintain the Health Score chart of the patient, including collecting historical data, performed at step 240.

In some embodiments of generating a Health Score chart, the patient data that may be collected by collection module 54 of system 50 may include both subjective and objective data. Although objective data has been used in the past to generate a single number representing a patient's health, subjective data, such as nursing assessments, may be very significant in predicting the health of a patient. These subtle measurements, which use a nurse's insights and skills, are important in determining the patient's risk. Physicians frequently overlook this information, yet its inclusion increases the robustness of the Health Score, and provides a channel for nurses to more effectively convey information to physicians. Subjective data may include variables, which may require human evaluation or assessment, rather than collecting a numerical value, such as blood pressure, heart rate, and other measurable factors. On some embodiments, subjective data includes information commonly collected in nursing assessments. In some embodiment, the information as to if a patient has met a particular standard (such as are listed below) may not be available. In that case, data is taken from the medical record (whether on paper or in electronic form) so as to determine if such a standard would have been met. Examples of subjective data may include standards which are determined by a nurse after assessing a variety of factors in a category, such as cardiac standard (which may be include factors, such as pulse rate in beats per minute, warmth and dryness of skin, blood pressure, and/or symptoms of hypotension), food/nutrition standard ((which may be include factors, such as ability to chew and/or swallow, manual dexterity, and/or consumption of daily diet as ordered, observed or stated), gastrointestinal standard (which may be include factors, such as feel and appearance of the abdomen, bowel sounds, nausea or vomiting, continence and/or bowel patterns), genitourinary standards (which may be include factors, such as voids, continence, urine color and/or smell as observed or stated, and/or urinary catheter), musculoskeletal standards (which may be include factors, such as ability to move all extremities independently and/or perform functional activities as observed or stated, including use of assistive devices), neurological standards (which may be include factors, such as alertness, orientation to persons, place, time and situation and/or speech coherence), pain standard (which may be include factors, such as pain/VAS level and/or chronic pain management), peripheral vascular standard (which may be include factors, such as normal appearance and feel (e.g., warm and pink) of extremities, capillary refill, peripheral pulses, edema, numbness and/or tingling), psycho-social standard (which may be include factors, such as appropriateness of behavior to situation, expressed concerns and fears being addressed and/or support system), respiratory standard (which may be include factors, such as respirations at rest, bilateral breath sounds, nail beds and mucous membranes, and/or look and feel of sputum), safety/fall risk standard (which may be include factors, such as risk of patient to self and/or others), and/or skin/tissue standard (which may be include factors, such as skin CD&I, reddened areas, alertness, cooperation and ability to reposition self independently, and/or Braden scale). In some embodiments any or all of the above standards can be determined by a nurse using a pass/fail system. Even though these standards may be binary assessments, the transition from passing a standard to failing a standard can be very predictive in indicating the health of a patient. For example, if a patient moves from failing two standards, to failing five standards, to failing 7 standards, the patient may be going through a very serious decline in health, even if the patient's vital signs are relatively normal or not changing.

This information can be collected in any way, such as a nurse filling out a checklist on a clipboard, entering the data directly into a computer, PDA, a handheld electronic device or any other device, as not all embodiments are intended to be limited in this respect. In additional or alternatively, these determinations may be made by means other than healthcare workers, such as by a smart bed or another device which can provide an electronic assessment.

In some embodiments, additional data from a healthcare provider's notes may be incorporated as data. For example, a patient may have passed the respiratory standard of a nursing assessment, but the nurse may have indicated a notation of "diminished breathing capacity." This note may be incorporated into the nursing assessment analysis or as a separate variable as not all embodiments of the present disclosure are intended to be limited in this respect.

In some embodiments of the present disclosure, a single term in the Health Score formula may contain multiple medical data inputs. For example, as noted in the above incorporated discussions of Heath Score, various medical readings (e.g. blood pressure, heart rate, and similar readings) are each transformed into a particular number which are combined to form the plotted Heath Score chart. It is understood however, the multiple medical data inputs may be combined before being transformed, such that the transformed number used for forming a portion of the Heath Score, may be a combination of multiple health readings. For example, systolic and diastolic blood pressure may be combined into a single number before being transformed for use in the Heath Score. Factors used in determining the Health Score may include objective and subjective factors, such as diastolic blood pressure, systolic blood pressure, temperature, pulse, respiration rate, a pain score, weight, skin breakdown score, EKG pattern, and a set of nursing assessments, as described above. Thus, collection module 54 may obtain both past and present data necessary for the patient on each of the categories to form the Health Score chart. Other inputs into the system may include weight, height, body mass index, or any other variables as not all embodiments of the present disclosure are intended to be limited in this manner.

The raw data may be transmitted to transformation module 56, and the historical data is sent to presentation and/or comparison module 60.

Next, at step 250, transformation module 56 transforms the raw patient medical data into a usable format, so that all of the disparate forms of medical data can readily be compiled with one another. Transformation module 56 may be configured to transform each of the pieces of medical data obtained from collection module 54 into a numerical quantity at step 250. The transformation performed by module 56 may include any number of mathematical or logical operations. Transformations may also take multiple inputs to produce a single transformed output. Multiple inputs may include historical data for this patient or for any given class of patients. Thus, transformation module 56, after receiving raw data from collection module 54, may process the data and transforms them into numbers for use in generating a Health Score for the patient. In an embodiment, transformation module 56 converts each of the patient's medical data to Health Score values using a set of functions stored in the memory of system 50. These stored functions define excess risk due to deviation from normative values for each of the medical data.

The above conversions of medical data into scaled numbers is geared to assessment of negative factors. However, it is understood that positive assessments may be included too, resulting in "negative" scaled numbers, that would show a positive affect on the Health Score. For example, transformation module 56 may give a negative scaled number in the event that heart rate or lung capacity or other such medical data is not only OK, but is in fact at an ideal state.

At step 260, the transformed medical data is sent to combination module 58, which converts that raw transformed medical data into a Health Score using a predetermined algorithm. Combination module 58 may be configured to take the transformed quantities from transformation module 56, apply weighting modifiers, and to combine them, and then to scale them onto a range, such as a score between 0 and 100, at step 260. This score, generated by combination module 58, is based on the various health factors measured and transformed above, the resulting score being a relative overall Health Score of the patient being monitored.

In an embodiment, weighting factors (2 times, 3 times, and more) can be added or multiplied to certain transformed numbers, such as the respiratory factors, when a particular patient is recovering from a lung-based ailment such as pneumonia. Likewise, similar weighting factors can be added to the transformed scores of heart rate, heart rhythm, systolic and diastolic pressure for patients with heart ailments. It is understood that any number of modifications introduced into a similar combination module 58 within a similar system 50 for generating a Health Score is within the contemplation of the present disclosure.

At step 270, the Health Score is transmitted to presentation and/or comparison module 60, which uses the current Health Score, as well as historical data from storage module 64 (past Health Scores), to generate a Health Score chart 80.

Presentation and/or comparison module 60 of system 50 may be configured to import the various data components compiled by combination module 58 and to create a Health Score chart for the patient at step 270, and may display it via interface module 52 of system 50, or on an existing medical information system, such as the hospital's pre-existing computer system. In some embodiments, the presentation and/or comparison module 60 may include a statistical reference curve on said Heath Score plot, so that the Health Score may be easily compared to an average patient with similar conditions and circumstances. In some embodiments, the presentation and/or comparison module 60 may supply principal corresponding measurements of direct raw medical data on said Heath Score chart, may provide a smoothed Heath Score curve, alongside said Heath Score plot that provides a running average of the Health Score plot over time and/or may supply the curvature of a smoothed Health Score plot.

Health Score chart may be for displaying the Health Score of a patient at particular times, and more importantly, may be for detecting trends in a patient's health. Thus, Health Score chart may include a number of Health Score assessments taken frequently, both at periodic (e.g. every 15 minutes, or every 3 hours), or at irregular intervals. For example, the Health Score of a patient may be computed ten or more times a day, approximately every 2 hours over the course of a six-day stay.

Comparison module 60 may be used to generate and present pre-operation reference curves. Information from pre-operation may be posted on the patient's Health Score chart so as to give additional context to their condition. For example, before an operation, the patient may have exhibited a Health Score of 50. After the operation, the doctors may expect the patient to be significantly better. Since before the operation he had a Health Score of 75, we expect that, although he will go through some difficult periods during recovery, he will get back to 75 within a week. This acts as a baseline reference, to help better personalize the chart to each patient.

Statistical reference curves may also be added to Health Score chart by comparison module 60. For example, when such information is available, statistically computed average patient Health Score trajectories, for each specific procedure and initial patient condition, may be included on chart next to the Health Score plot. This information may be stored in a storage module 64, and may be imported into comparison module 60 by collection module 54. Statistical reference curves may include linear information with standard deviation error bars or transformed values. If the patient is below expectation by a certain number of standard deviations, the system generates an alert using alert module 62, as discussed below.

Further subdivisions can also be made for such statistical reference curves. For example, instead of having a single reference curve for average open-heart patients of age 80, it can be further broken down by gender, and even further modified as to a patient's initial condition by using only patients with similar Health Scores at the time of admission into the hospital.

Principal corresponding measurement curves may also be generated by comparison module 60 of system 50. The Health Score chart may provide an instant context and patient health trajectory on Health Score plot. It is also important for healthcare providers to have access to other direct measurements, including, but not limited to, diastolic blood pressure, temperature, respiration rate, pulse, and pain score. This allows healthcare providers to detect other trends that may be affecting the Health Score and, thus, the patient. It is understood that, when using the option of adding direct medical data to the Health Score chart, system 50 has the ability to let the healthcare provider select which principal corresponding measurements they would like to see. When the Health Score is improving or is adequate, such features may be toggled off, as they are less important in such instances. They can easily be added to chart if the score on the plot again drops, allowing the healthcare provider, optionally, to have additional analysis tools for determining the cause of the drop.

In another embodiment, presentation and/or comparison module 60 may be configured to alter Health Score chart, so that when a healthcare provider detects a trend in the Health Score plot, they can understand exactly what factors are contributing. To this end, system 50 may provide for a component expansion window, such that if the patient has a Health Score of 65 (for example), the expansion might show that the patient lost 12 points due to elevated temperature (over 101 Fahrenheit), lost 18 points due to rapid pulse (between 100 and 110 beats per minute) and lost 5 points due to a pain score of 5; all out of the perfect Health Score of 100.

In another embodiment, presentation and/or comparison module 60 may also alter Health Score chart to obtain certain kinds of slope information. Even though trends are usually easy to spot by eye upon looking at Health Score plot, an automatic "simple" slope calculation may also be useful. Mathematically, this is the first derivative of the Health Score as a function of time. Due to the "noisiness" of typical Health Score plots some averaging methods may be employed as well. If the slope is positive, the patient is probably getting better; if it is approximately zero, then the patient is staying the same; and if it is negative, then the patient is probably getting worse. Slope lines may be added to the Health Score plot Such slope information may help identify trends in Health Score plot, particularly, when the plot is "noisy" due to large variations between each Health Score measurement. Although normally "staying the same" would not be considered a negative, in the situation where the patient is expected to be recuperating, "staying the same" may be quite worrisome.

Presentation and/or comparison module 60 of system 50 may also compute "rate of change" of the simple slope. For instance, although the patient is still getting better, the rate of improvement may be decreasing. This slow-down in recovery could be evidence of a problem just beginning to develop. Mathematically, this curvature information is the second derivative of Health Score as a function of time. Similar to the slope data, due to the "noisiness" of the curves, averaging is included in the computation. It is understood that attending physicians can adjust the slope calculation to include more or less reference Health Scores from the plot depending on the time span over which the physician intends to analyze.

The Health Score may be calculated continuously for a patient's entire hospital stay and/or recovery period and any or all of that information may be displayed on the screen. In some embodiments, the graph may display the patient's Health Score during his/her entire hospital stay, thereby enabling the healthcare provider to look at one screen and be able to understand the patient's health history, as opposed to having to flip through hundreds of pages of a patient's medical history. In some embodiments, the time span over which the Health Score is plotted may be a patient's entire hospital stay, the patient's stay in a certain ward, such as the ICU or ER, the past few days of the patient's stay, a number of hours (such as 3, 5, 10, 12, 13 or more hours), days, weeks or months, or any length of time as not all embodiments are intended to be limited in this respect. In some embodiments, the chart may contain compressed or selective data from a period of time and full data from a different period of time. For example, if a patient has been in a hospital for a month, the most recent three days may be depicted by hourly Health Scores, while the rest of the month, prior to those three days, may be depicted by a daily summary point on the chart.

When the raw data is noisy, a "running average" or other "smoothing" of the Health Score can be displayed on Health Score charts. The smoothed Health Score curve could incorporate both the $1^{st}$ derivative (slope) and/or the $2^{nd}$ derivative (curvature) by color-coding or by thickness of the displayed line. For example, if the patient was getting worse (negative slope), the line might be colored red. If the patient is getting worse at an accelerating rate, or is getting better at a lessening rate, then the line could be bolded for emphasis.

Presentation and/or comparison module 60 may further display a panel of Health Score charts. Typically, a nurse or a doctor or a unit supervisor wants to see, on a single page, the graphs for all the patients in their care. Therefore, system 50 may provide for the creation of a patient panel, displaying a series of Health Score charts. Patient IDs can be included in the label data to identify each chart on the panel. This is especially useful because an attending physician may wish to appoint more of his time to patients with falling Health Scores (rather than rising ones), given that those patients with falling scores will likely require more attention and given that the physician's time is usually very limited.

It is understood that such modifications to patient Health Score charts are intended only as example modification and are in no way intended to limit the scope of the present disclosure. Any similar disclosure that utilizes modified Health Score charts is also within the contemplation of the present disclosure.

At step 280, after the Health Score chart 80 has been generated, presentation and/or comparison module 60 may modify and display the Health Score chart 80 to healthcare providers, via interface module 52 of system 50. At step 290, presentation and/or comparison module may further save any necessary information to storage module 64.

At step 291, if the Health Score falls below a predetermined threshold, alert module 62 may inform the healthcare providers, either through interface module 52 or via some other alarm, that the patient is in need of attention. For example, if an attending physician sets a threshold of 70, then patients falling below such a level may cause alert module 62 to send an alert message to a system terminal at a nursing station. Although the physician may wish to see Health Score charts, regardless of the alerts, alert module 62 may act as a reserve precaution warning of the general failing health conditions of a patient who may be approaching a crisis situation. It is understood that the alert may actually be set to an upper threshold as well. Keeping physicians aware of improving health conditions of certain patients may be useful in making discharge decisions or in adjusting medication. Alerts may also be triggered by a fall of so many points in Health Score or by a slope that is of a sufficient negative magnitude.

It is noted that the above list of steps for generating a Health Score chart via system 50 is intended only to show an exemplary step-by-step process. For example, several of the steps may be combined with one another or possibly one step may be divided into a number of subroutines. Any similar process using steps to create a Health Score chart on a similar system is also with in the contemplation of the present disclosure.

Figure 11:
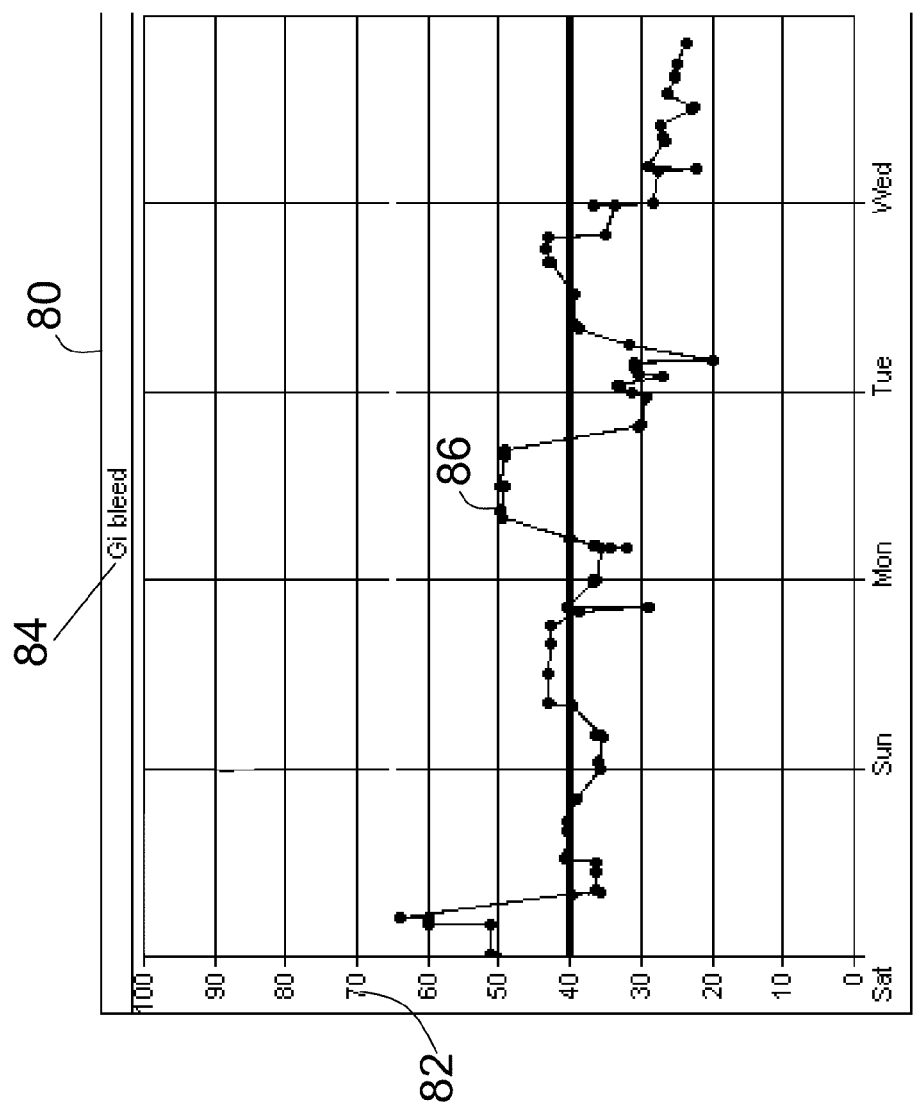
FIG. 11 is a chart showing a patient's Health Score derived using a method of the present disclosure.

A sample Health Score chart 80 is shown in FIG. 11, plotting a patient's Health Score, calculated by system 50 as a function of time. The chart 80 includes scale markings 82 and label material 84 and a Health Score plot 86. The chart 80 shows a sample Health Score plot 86 for a patient who experienced a gastrointestinal (GI) bleed. During a GI bleed, the amount of bleeding can range from nearly undetectable to acute, massive, and life threatening. At the beginning of this graph (which is the first of the 5 days represented), the patient had a Health Score in the low 50s. Shortly thereafter, the patient's Health Score improved to a value in the 60s. However, at some point on the first day, the Health Score began to decline, e.g., the Health Score quickly went from a value in the 60s to a value in the 30s. It is at this particular moment, at the middle of the first day, that the Health Score chart 80 can prove to be a critical tool for medical care. With the Health Score chart 80 available, it would be obvious to a physician or nurse that something is going wrong with the patient at the end of day 1. This is a critical time for the patient, because immediate treatment may prevent a crisis.

Figure 12:
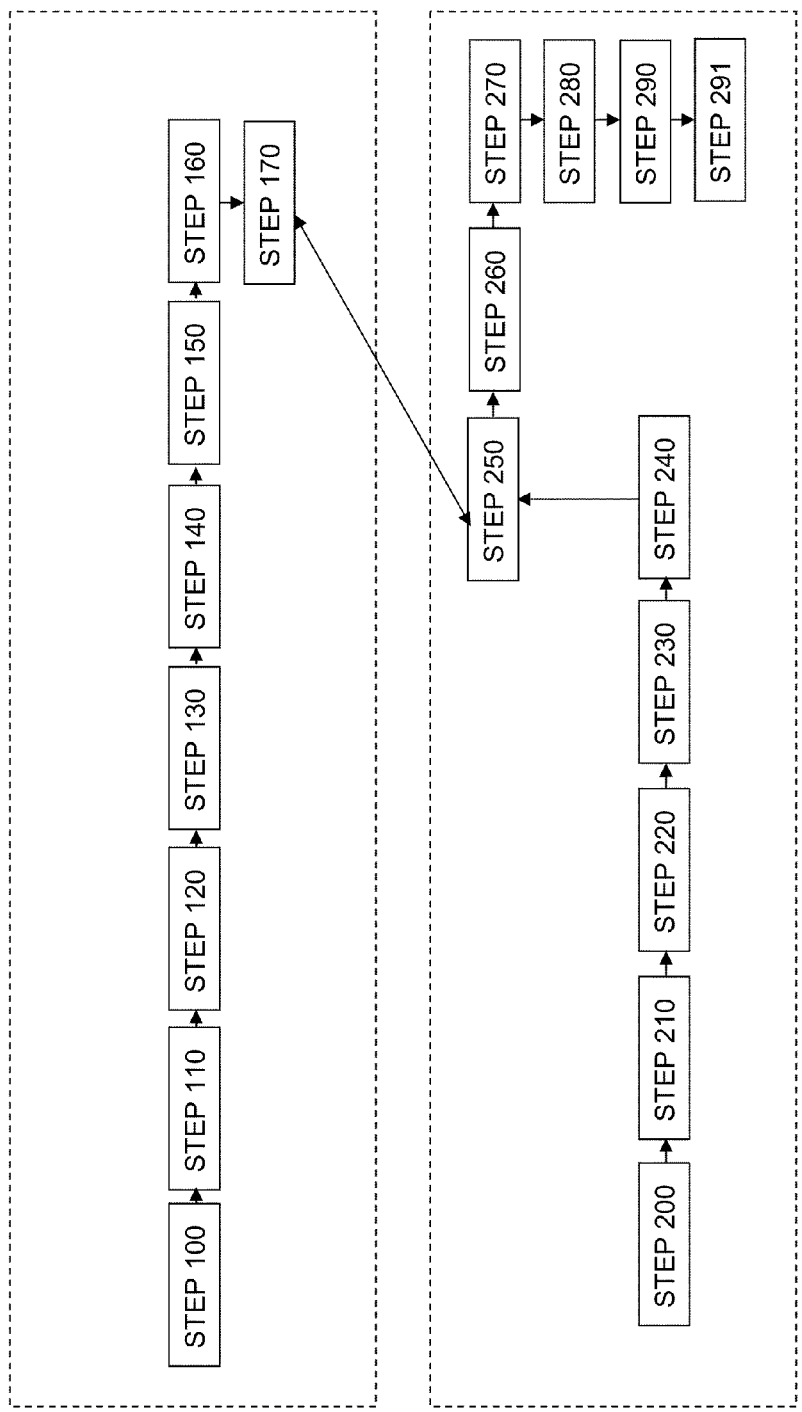
FIG. 12 is a flow chart showing the relationship between the method steps performed to define risk associated with medical data (as described in FIG. 1), and the method steps performed to determine an overall risk inherent in a patient's current condition (as described in FIG. 10).

As described above, Health Scores for an admitted patient are generated by computing excess risk due to deviation from normative values, as a function of each type of medical data measured against one-year mortality. To provide the Health Score with continuous input functions for each type of medical data, average one-year mortality versus averages of each type of medical data for distinct ranges, were fit to higher-order polynomials based on data obtained from an EMR for a plurality of different patients. FIG. 12 is a flow chart showing the relationship between the top flow path which shows the method steps performed to define excess risk due to deviation from normative values for at least one type of medical data (as described in FIG. 1), and the bottom flow path which shows the method steps performed to determine an overall risk inherent in a patient's current condition (as described in FIG. 10). It should be understood that the top flow path and the bottom flow path do not necessarily occur at the same time. In an embodiment, the top flow path occurs first (steps 100-170), wherein functions are derived for assessing excess risk associated with the medical data, and the data and/or functions are stored within system 50 for later use in determining the Health Score(s) of the admitted patient. In step 100, the same type of medical data collected at a first time from a plurality of patients is collected from an electronic medical record (EMR) by a computer. In step 110, an outcome measurement derived from a second time for each of the plurality of patients is obtained by a computer. In step 120, a dataset representing each of the plurality of patients is created by a computer. The dataset includes (x,y) pairs for each patient, wherein x is the type of medical data at the first time, and wherein y is the outcome measurement at the second time. In step 130, the (x,y) pairs are ordered by a computer. In step 140, the (x,y) pairs are binned by a computer to form a plurality of binned data sets. In step 150, an average value for x (x_bar value) and an average value for y (y_bar value) for each binned data set is computed by a computer. In step 160, the minimum average value of y_bar (y_bar (min)) is subtracted from each y_bar value, resulting in a new average value for y_bar for each binned data set. In step 170, a function y=f(x) for assessing excess risk associated with the medical data is derived.

In step 200, a patient is admitted for a particular illness or surgical procedure and is subsequently connected to system 50. At step 210, various medical devices/monitors for obtaining the pertinent raw medical data can be attached to the patient, such as blood pressure monitors, heart rate monitors, and similar devices. At step 220, interface module 52 begins obtaining the pertinent raw medical data about the patient and imports this data into system 60. At step 230, the data may be sent to collection module 54. At step 240, collection module 54 may further obtain any necessary past medical data, most importantly the past Health Scores of the same patient. Next, at step 250, transformation module 56 transforms the raw patient medical data into a usable format, so that all of the disparate forms of medical data can readily be compiled with one another. The transformation module 56 converts raw medical data into scaled numbers based on the function derived at step 170. In an embodiment, the function(s) are stored in storage module 64. In an embodiment, the functions are stored in the memory of system 50. In an embodiment, the functions are stored in the memory of another computer that is in communication with system 50. At step 260, the transformed medical data is sent to combination module 58, which converts that raw transformed medical data into a Health Score using a predetermined algorithm. Presentation and/or comparison module 60 of system 50 may be configured to import the various data components compiled by combination module 58 and to create a Health Score chart for the patient at step 270, and may display it via interface module 52 of system 50, or on an existing medical information system, such as the hospital's pre-existing computer system. At step 280, after the Health Score chart 80 has been generated, presentation and/or comparison module 60 may modify and display the Health Score chart 80 to healthcare providers, via interface module 52 of system 50. At step 290, presentation and/or comparison module may further save any necessary information to storage module 64. At step 291, if the Health Score falls below a predetermined threshold, alert module 62 may inform the healthcare providers, either through interface module 52 or via some other alarm, that the patient is in need of attention.

In one embodiment, fifty potential variables may be used from data readily available in the patient's records. For some or all potential variables, excess risk as a function of the variable may be computed, as measured by one-year mortality. The computed excess risk may be the additional mortality risk above the risk for the variable's minimum mortality. In order to provide the Health Score with continuous input functions of each of these variables, the plots of 1-year mortality may be compared with each variable to higher order polynomials. With all variables on a common risk scale, the relative importance of variables may be determined by using stepwise logistic regression. Two variable sets (with a total of twenty-six variables) may be built, one which incorporates data inputted approximately every 4-6 hours (vital sign and nursing assessments) and the other including data from blood chemistry panels and blood analysis.

Each set of variables may be used to construct a model scaled from zero to 100, so that the best health would be represented by a value of 100 and the worst health be represented by a value of zero. The Health Score may consist of a linear combination of these two models weighted by two factors: a scaling factor, to bring the absolute values of the two models into alignment, and a time-dependent factor, used to determine the proportion of the more slowly refreshed chemistry panel model, whose contribution decays to zero over 48 hours as the data ages.

The Health Score may use 26 variables, for example, vital signs, including temperature, systolic blood pressure, diastolic blood pressure, heart rate, blood oxygen saturation and respiratory rate; nursing assessments, including cardiac, food/nutrition, gastrointestinal, genitourinary, musculoskeletal, neurological, peripheral vascular, psycho-social, respiratory, skin/tissue and safety/fall risk standards; scores, including Braden Scale Heart patterns; blood chemistry, including blood urea nitrogen, creatinine, chloride, sodium and potassium; and blood analysis, including hemoglobin and white blood cell count.

As such, the above-described system 50 and accompanying generated Health Score charts may provide a convenient means for monitoring patient health status, particularly in hospital post-operational situations. It may allow doctors to get a feel for the overall health of the patient and to detect trends in the patient's health. Such information is particularly useful in preventing crisis situations from arising in patients, where the worsening condition (of a patient of adequate, yet deteriorating health) is overlooked until it is too late. The creation of the Health Score chart, by the present disclosure, may help in alerting attending physicians, nurses, or "rapid response teams" to deteriorating conditions, even when a spot check of the patient's health would seem to show the patient to be in an adequate state of health.

In addition to the uses outlined above, the Health Score can be used for statistical analysis. For example, the Health Score and the Health Score charts can be used in retrospective research. Many studies of drugs and procedures are published monthly. These studies would benefit from the inclusion of a readily computable Health Score.

For example, a procedure is often evaluated in terms of mortality rate, length of hospital stay, or number of re-admissions to the hospital. These measures are all significant, but at the same time are all rather crude measures. For example, if "Procedure A" has a mortality rate of 0.5% and "Procedure B" has a mortality rate of 0.7%, it may be very difficult to judge one the superior of the other, using only these mortality statistics. However, if patients discharged after Procedure A have an average Health Score of 80, and those discharged after Procedure B have an average Health Score of 60, there may be a real and meaningful difference between the two procedures in terms of overall efficacy in treating the patient. Thus, system 50 may provide a more sensitive measurement of health than any other available measure, since it is not based solely on major "outcomes" (like discharge or death), but rather on a more subtle combination of overall health factors. A medical study using the Health Score, which this disclosure makes readily available for every patient, may find earlier and easier and more meaningful "statistical significance" than a similar study that needed to wait for eventual mortality outcomes.

An additional feature of Health Scores generated by system 50 is that the Health Score can be used as a predictor to assist in determining which patients require the most care. Although individual symptoms and raw medical data may be varied, the amalgamated Health Score, as shown on Health Score charts, tends to be an accurate predictor of patient outcome. Furthermore, incoming Health Scores can be used as an indicator of survival rates before undergoing certain procedure. Not all patients are equal when entering the hospital for a procedure. In some cases, a decision "not to operate" may be made if the risks of complication are too great. An admission-timed Health Score from system 10 may also provide statistical information for post-operative survival rates, which could greatly influence a hospital's decision to recommend the use of surgery, versus alternative treatments.

In some embodiments, the system 50 may allow physicians and nurses and clinical researchers to provide more effective health care for each patient, especially those spending several days in a hospital. In some embodiments, hospitals may avoid errors and reduce crisis management by using the system's ability to detect trends in a patient's health before the patient reaches a crisis point. Recognizing a serious decline soon enough to administer proper treatment may be a life-saving benefit. In some embodiments, the system may give physicians and nurses a way in which to get the "big picture" of a patient's condition and absorb in a glance perhaps 100 pages of a patient's medical records. This deeper understanding, along with this new capability to detect health trends, both short-term (over the space of hours), and long-term (over the space of days), may be important in delivery of effective medical care. In some embodiments, an entirely new field of scientific study may be enabled, where medical and surgical treatments can be evaluated by the new measurements provided by some of the systems disclosed herein A method of assessing risk associated with medical data includes creating, by a computer, a dataset representing a plurality of patients, the dataset comprising (x,y) pairs for each patient, wherein x represents the medical data collected at a first time, and wherein y is an outcome measurement collected at a second time; binning, by a computer, the (x,y) pairs to form a plurality of binned data sets; computing, by a computer, an average value for x and an average value for y for each binned data set; determining, by a computer, a minimum average value of y based on all of the average values of y; subtracting, by a computer, the minimum average value of y from each average value of y to get a new average value of y for each binned data set; and deriving, by a computer, a function for assessing risk associated with the medical data. In an embodiment, the deriving of the function includes computing, by a computer, a first function defined from average minimum value of x to average maximum value of x; adding, by a computer, a second constant function to the first function, wherein the second constant function covers values of x less than the average minimum value of x; and adding a third constant function to the first function and the second constant function, wherein the third constant function covers values of x greater than the average maximum value of x.

A method of determining an overall risk inherent in a patient's current condition includes receiving, by a computer, a plurality of medical data from an admitted patient; converting, by a computer, each of the admitted patient's medical data to Health Score values using a set of functions, wherein each of the functions defines risk associated with each of the medical data; combining, by a computer, the Health Score values; generating, by a computer, a Health Score from the combined data, the Health Score representing the admitted patient's health; and displaying, by a computer, the Health Score. In an embodiment, the set of functions is derived using the following steps: (a) creating, by a computer, a dataset representing a plurality of discharged patients, the dataset comprising (x,y) pairs for each patient, wherein x represents a single type of medical data collected at a first time, and wherein y is an outcome measurement collected at a second time; (b) binning, by a computer, the (x,y) pairs to form a plurality of binned data sets; (c) computing, by a computer, an average value for x and an average value for y for each binned data set; (d) determining, by a computer, a minimum average value of y based on all of the average values of y; (e) subtracting, by a computer, the minimum average value of y from each average value of y to get a new average value of y for each binned data set; (f) deriving, by a computer, a function for assessing risk associated with the single type of medical data; and (g) repeating steps (a)-(f) for other types of medical data to derive the set of functions. In an embodiment, the method further includes making a healthcare decision based on the Health Score. In an embodiment, the Health Score reflects the risk inherent in an admitted patient's current condition. In an embodiment, the Health Score correlates with various measures of patient risk or vitality, such as: the likelihood of dying in 48 hours, the likelihood of returning to the hospital within 90 days, the likelihood of dying in the ICU, and the effectiveness with which classes of discharge disposition can be separated.

A method of assessing excess risk associated with medical data includes creating, by a computer, a dataset representing a plurality of patients, the dataset comprising (x,y) pairs for each patient, wherein x represents the medical data collected at a first time, and wherein y is an outcome measurement collected at a second time; binning, by a computer, the (x,y) pairs to form a plurality of binned data sets; computing, by a computer, an average value for x and an average value for y for each binned data set; determining, by a computer, a minimum average value of y based on all of the average values of y; subtracting, by a computer, the minimum average value of y from each average value of y to get a new average value of y for each binned data set; and deriving, by a computer, a function for assessing excess risk associated with the medical data. In an embodiment, the deriving of the function includes computing, by a computer, a first function defined from average minimum value of x to average maximum value of x; adding, by a computer, a second constant function to the first function, wherein the second constant function covers values of x less than the average minimum value of x; and adding a third constant function to the first function and the second constant function, wherein the third constant function covers values of x greater than the average maximum value of x.

In an embodiment, the methods disclosed herein can transform data representing physical objects (i.e., medical data from a patient) into risk associated with medical data that may be visually displayed. In an embodiment, the methods disclosed herein can transform data representing physical objects (i.e., medical data from a patient) into Health Scores that may be visually displayed. The embodiments described herein may be implemented using any appropriate computer system hardware and/or computer system software. In this regard, those of ordinary skill in the art are well versed in the type of computer hardware that may be used (e.g., a mainframe, a mini-computer, a personal computer ("PC"), a network (e.g., an intranet and/or the internet)), the type of computer programming techniques that may be used (e.g., object oriented programming), and the type of computer programming languages that may be used (e.g., C++, Basic, AJAX, Javascript). The aforementioned examples are illustrative and not restrictive. For purposes of this disclosure, a computer or computing device includes a processor and memory for storing and executing program code, data and software which may also be tangibly stored or read from any type or variety of well known computer readable storage media such as magnetic or optical discs, by way of non-limiting example. Computers can be provided with operating systems that allow the execution of software applications in order to manipulate data. Personal computers, personal digital assistants (PDAs), wireless devices, cellular telephones, internet appliances, media players, home theater systems, servers, and media centers are several non-limiting examples of computing devices. The computer or computing device can also include a display, such as a screen or monitor.

For the purposes of this disclosure, a computer readable medium is a medium that stores computer data in machine readable form. By way of example, and not limitation, a computer readable medium can comprise computer storage media as well as communication media, methods or signals. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology; CD-ROM, DVD, or other optical storage; cassettes, tape, disk, or other magnetic storage devices; or any other medium which can be used to tangibly store the desired information and which can be accessed by the computer.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of assessing risk associated with medical data comprising:
   creating, by a computer, a dataset representing a plurality of patients, the dataset comprising (x,y) pairs for each patient, such that x represents the medical data collected at a first time, y is an outcome measurement collected at a second time, and the collected medical data is selected from one of a continuous variable or an ordinal score;
   binning, by a computer, the (x,y) pairs to form a plurality of binned data sets;
   computing, by a computer, an average value for x and an average value for y for each binned data set;
   determining, by a computer, a minimum average value of y based on all of the average values of y;
   subtracting, by a computer, the minimum average value of y from each average value of y to get a new average value of y for each binned data set; and
   deriving, by a computer, a first function for assessing risk associated with the medical data, such that the first function is defined from a minimum average value of x to a maximum average value of x;
   deriving, by a computer, a second function for assessing risk associated with values of x less than the minimum average value of x; and
   deriving, by a computer, a third function for assessing risk associated with values of x and greater than the maximum average value of x,
   wherein the derived functions are used in calculating the risk associated with the medical data.

2. The method of claim 1 wherein the medical data for each patient is collected at discharge of the patient from a facility of care.

3. The method of claim 1 wherein the outcome measurement represents a mortality of each of the patients.

4. The method of claim 1 wherein the outcome measurement for each patient is collected one-year post discharge.

5. The method of claim 1 wherein the functions define excess risk due to deviation from normative values.

6. The method of claim 1 wherein the continuous variables are selected from the group consisting of albumin/globulin (A/G) ratio, an alanine aminotransferase (ALT or SGPT) value, an aspartate aminotransferase (AST or SGOT) value, an albumin value, an alkaline phosphatase value, a blood urea nitrogen (BUN) value, a calcium value, a carbon dioxide ($CO_2$) value, a chloride value, a creatinine value, a globulin value, a glucose value, a potassium value, a sodium value, a total bilirubin value, a total protein value, a tropon value, a base excess value, a fraction of inspired oxygen ($FiO_2$) value, a bicarbonate ($HCO_3$) value, a partial pressure of carbon dioxide ($PCO_2$) value, a partial pressure of oxygen ($PO_2$) value, a pH value, a hematocrit percentage, a hemoglobin value, a white blood cell count, a heart rate value, a diastolic blood pressure value, a systolic blood pressure value, a respiration rate, a percentage of arterial hemoglobin in oxyhemoglobin configuration (pulse Ox) and a temperature value.

7. The method of claim 1 wherein the ordinal score is a Braden Scale score.

8. The method of claim 1 wherein the derived functions are used in calculating an overall risk inherent in a patient's medical condition.

9. The method of claim 1 wherein the derived functions can be used in determining a risk inherent in a value of corresponding medical data from a patient.

10. A method of determining an overall risk in a patient's current condition comprising:
    receiving, by a computer, a plurality of medical data about a patient at a plurality of time points over a period of time, such that the received medical data includes continuous variables;
    converting, by a computer, each of the admitted patient's medical data for each of the plurality of time points to values using a set of functions, wherein each of the functions defines risk associated with each of the medical data, and wherein the set of functions for each of the medical data is derived by:

creating, by a computer, a dataset representing a plurality of discharged patients, the dataset comprising (x,y) pairs for each discharged patient, such that x represents a single type of medical data collected at a first point in time and y is an outcome measurement collected at a second point in time;

binning, by a computer, the (x,y) pairs to form a plurality of binned data sets;

computing, by a computer, an average value for x and an average value for y for each binned data set;

determining, by a computer, a minimum average value of y based on all of the average values of y;

subtracting, by a computer, the minimum average value of y from each average value of y to get a new average value of y for each binned data set;

deriving, by a computer, a first function for assessing risk associated with the medical data, such that the first function is defined from a minimum average value of x to a maximum average value of x;

deriving, by a computer, a second function for assessing risk associated with values of x less than the minimum average value of x; and deriving, by a computer, a third function for assessing risk associated with values of x and greater than the maximum average value of x;

combining, by a computer, for each of the plurality of time points, the values;

generating, by a computer, a Health Score from the combined values for each of the plurality of time points, each Health Score representing the patient's health; and continually displaying, by a computer, a graph of each of the Health Scores, wherein the derived functions are used in calculating the overall risk in the patient's current condition.

11. The method of claim 10 wherein the medical data for each discharged patient is collected at discharge of the patient from a facility of care.

12. The method of claim 10 wherein the outcome measurement represents a mortality of each of the discharged patients.

13. A method of defining excess risk associated with medical data comprising:

creating, by a computer, a dataset representing a plurality of patients, the dataset comprising (x,y) pairs for each patient, such that x represents a pass or a fail score of a nursing assessment collected at a first point in time and y is an outcome measurement collected at a second point in time;

binning, by a computer, the (x,y) pairs to form two binned data sets;

computing, by a computer, an average value for y for each binned data set;

determining, by a computer, a minimum average value of y based on all of the average values of y;

subtracting, by a computer, the minimum average value of y from each average value of y to get a new average value of y for each binned data set; and calculating, by a computer, a function for defining excess risk associated with the failing of the nursing assessment, wherein the calculated function is used in determining the excess risk associated with the medical data.

14. The method of claim 13 wherein the nursing assessment is selected from a food assessment, a neurological assessment, a psychiatric assessment, a safety assessment, a skin assessment, a genitourinary assessment, a musculoskeletal assessment, a respiratory assessment, a cardiac assessment, a peripheral vascular assessment, a gastrointestinal assessment and a pain assessment.

15. The method of claim 13 wherein the nursing assessment for each patient is collected at discharge of the patient from a facility of care.

16. The method of claim 13 wherein the outcome measurement represents a mortality of each of the patients.

17. The method of claim 13 wherein the outcome measurement for each patient is collected one-year post discharge.

18. The method of claim 10 wherein the second function and the third function are constant functions.

19. The method of claim 10 wherein the received medical data further includes nursing assessments.

20. The method of claim 19 wherein each of the nursing assessments are converted, by a computer, to values using a set of functions, wherein each of the functions defines an excess risk associated with failing of a nursing assessment, and wherein each function is derived by:

creating, by a computer, a dataset representing a plurality of patients, the dataset comprising (x,y) pairs for each patient, wherein x represents a pass or a fail score of the nursing assessment collected at a first point in time, and wherein y is an outcome measurement collected at a second point in time;

binning, by a computer, the (x,y) pairs to form two binned data sets;

computing, by a computer, an average value for y for each binned data set;

determining, by a computer, a minimum average value of y based on all of the average values of y;

subtracting, by a computer, the minimum average value of y from each average value of y to get a new average value of y for each binned data set; and calculating, by a computer, the function for defining excess risk associated with the failing of the nursing assessment.

21. The method of claim 20 wherein the function is a constant function.

22. The method of claim 1 wherein the second function and the third function are constant functions.

23. A method of defining excess risk associated with medical data comprising:

creating, by a computer, a dataset representing a plurality of patients, the dataset comprising (x,y) pairs for each patient, such that x represents a categorical class determined at a first time and y is an outcome measurement collected at a second time;

binning, by a computer, the (x,y) pairs to form a plurality of binned data sets;

computing, by a computer, an average value for y for each binned data set;

subtracting, by a computer, the minimum average value of y from each average value of y to get a new average value of y for each binned data set; and calculating, by a computer, a function for defining excess risk associated with the categorical class, wherein the calculated function is used in determining the excess risk associated with the medical data.

24. The method of claim 23 wherein the categorical class is selected from the group consisting of sinus bradycardia, sinus rhythm, heart block, paced, atrial fibrillation, atrial flutter, sinus tachycardia and junctional rhythm.

25. The method of claim 23 wherein the function is a constant function.

* * * * *